United States Patent
Brooks et al.

(10) Patent No.: US 8,063,212 B2
(45) Date of Patent: Nov. 22, 2011

(54) IMIDAZOLIDINONYL AMINOPYRIMIDINE COMPOUNDS FOR THE TREATMENT OF CANCER

(75) Inventors: Harold Burns Brooks, Carmel, IN (US); Joyce Z. Crich, Indianapolis, IN (US); James Robert Henry, Indianapolis, IN (US); Hong-Yu Li, Zionsville, IN (US); Jason Scott Sawyer, Indianapolis, IN (US); Yan Wang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 293 days.

(21) Appl. No.: 12/516,251

(22) PCT Filed: Dec. 11, 2007

(86) PCT No.: PCT/US2007/087046
§ 371 (c)(1),
(2), (4) Date: May 26, 2009

(87) PCT Pub. No.: WO2008/076705
PCT Pub. Date: Jun. 26, 2008

(65) Prior Publication Data
US 2010/0081641 A1 Apr. 1, 2010

Related U.S. Application Data

(60) Provisional application No. 60/871,322, filed on Dec. 21, 2006.

(51) Int. Cl.
*C07D 401/00* (2006.01)
(52) U.S. Cl. ....................................... 544/331
(58) Field of Classification Search ............... 514/210.2, 514/275, 233.5; 544/331, 122
See application file for complete search history.

(56) References Cited

FOREIGN PATENT DOCUMENTS

| WO | 89/07599 | 8/1989 |
|---|---|---|
| WO | WO2004063192 | 7/2004 |
| WO | WO2004089913 | 10/2004 |
| WO | WO2006066172 | 6/2006 |
| WO | WO 2006066172 A1 * | 6/2006 |
| WO | WO2007092095 | 8/2007 |
| WO | WO2007117465 | 10/2007 |
| WO | WO2008076704 | 6/2008 |
| WO | WO2008144222 | 11/2008 |
| WO | WO2008144223 | 11/2008 |

OTHER PUBLICATIONS

B.C. Bastian, Genetic Progression From Melanocyte to Malignant Melanoma, in From Melanocytes to Melanoma the Progression to Malignancy 197, 201 (V. J. Hearing et al., eds., 2006).*
S. Cannistra et al, Ovarian Cander, Fallopian Tube Carcinoma and Peritoneal Carcinoma in, 1 Cancer Principles & Practice of Oncology 1568 (V.T. Deviata, Jr. et al. eds., 8th ed., 2008).*
K. G. Chen et al., How Melanoma Cells Evade Chemotherapy, in From Melanocytes to Melanoma the Progression to Malignancy 591 (V. J. Hearing et al., eds., 2006).*
I. Collins, Current Signal Transduction Therapy, 1, 13-23, 13 (2006).*
F.F. De Arruda, et al., Int. J. Radiation Oncology Biol. Phys., 64(2), 363-373 (2006).*
B. Hann et al., Current Opinion in Cell Biology, 13, 778-784 (2001).*
A. Kamb, Nature Reviews Drug Discovery 4, 161-165 (2005).*
S.K. Libutti, Colon Cancer in, Cancer Principles & Practice of Oncology 1232, 1243 (V.T. Deviata, Jr. et al. eds., 8th ed., 2008).*
K. Odunsi et al, Molecular Biology of Gynecological Cancers, in 1 Cancer Principles & Practice of Oncology 1487, 1492 (V.T. Deviata, Jr. et al. eds., 8th ed., 2008).*
K.P. Olive et al., Clinical Cancer Research 12, 5277-5287 (2006).*
L. Pusztai, Histopathologic and Molecular Markers of Prognosis and Response to Therapy, in Breast Cancer 324, 326-328 (Kelly k. Hunt et al., ed., 2nd ed., 2008).*
A.K. Rustgi, Molecular Biology of the Esophagus and Stomach, in 1 Cancer Principles & Practice of Oncology 989-993, 991 (V.T. DeVita, Jr. et al. eds., 8th ed., 2008).*
N.E. Sharpless et al., Nature Reviews Drug Discovery 5, 741-754, 742 (2006).*
N.F. Smith, Molecular Cancer Therapeutics, 6, 428-440, 428 (2007).*
Y. Song et al., Cancer a Conceptual Framework in, Cancer Principles & Practice of Oncology 1, 5-6 (V.T. Deviata, Jr. et al. eds., 8th ed., 2008).*

* cited by examiner

*Primary Examiner* — James O Wilson
*Assistant Examiner* — Alexander R Pagano
(74) *Attorney, Agent, or Firm* — Tina M. Tucker

(57) ABSTRACT

The present invention provides novel imidazolidinonyl aminopyrimidine compounds believed to have clinical use for treatment of cancer through inhibiting Plk1. Formula I wherein: $R^1$ is aminomethyl, $(C_1$-$C_3$ alkyl)aminomethyl, di($C_1$-$C_2$ alkyl)aminomethyl, N-ethyl-N-methyl-aminomethyl, 1-aminoethyl, 1-(($C_1$-$C_2$ alkyl)amino)-ethyl, 3,3,3-trifluoro-propylaminomethyl, ethynyl, 2-hydroxy-ethoxy, 2-hydroxyethylaminomethyl, 2-cyanoethylaminomethyl, morpholin-4-ylmethyl, methoxymethoxymethyl, cyclopropyl, 1-azetidinylmethyl, 1-pyrrolidinylmethyl, or 1,3-dioxolan-2-yl; $R^2$ is hydrogen or halo; $R^3$ is hydrogen or halo; provided that at least one of $R^2$ and $R^3$ is hydrogen; $R^4$ is hydrogen, methyl, or halo; and is a single bond that is either present or absent, or pharmaceutically acceptable salt thereof.

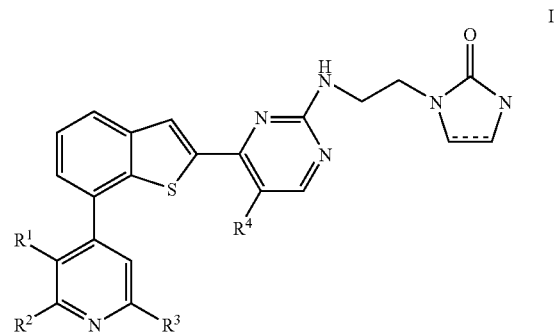

8 Claims, No Drawings

IMIDAZOLIDINONYL AMINOPYRIMIDINE COMPOUNDS FOR THE TREATMENT OF CANCER

This application claims the benefit under 35 U.S.C. §371 of International Application No. PCT/US2007/087046 filed Dec. 11, 2007 which claims benefit under 35 U.S.C. §119(e) of U.S. Ser. No. 60/871,322 filed Dec. 21, 2006.

BACKGROUND OF THE INVENTION

Plk1 belongs to a small family of protein kinases characterized by a phosphoserine/threonine binding domain known as the polo box domain. Plk1 plays a central role in the regulation of the cell cycle. Among other functions, Plk1 is thought to regulate initiation, progression, and exit from mitosis, the stage when cancer cells divide. Consequently, blocking Plk1 in cancer cells prevents their division or mitosis.

Potent anticancer agents have been identified that interfere with mitosis such as the vinca alkaloids (NAVELBINE®), taxoids (TAXOTERE®) and topoisomerase II inhibitors (ADRIAMYCIN®). VELCADE® is an antineoplastic agent that inhibits the 26S proteosome. However, these drugs cause considerable side effects upon normal, non-dividing cells. Plk inhibitors specifically target dividing cells and may be able to avoid the undesirable toxicities.

Inhibitors of Plk1 are known in the art. See for example, WO 06/066172. Additionally, WO 06/021548 discloses certain dihydropteridinone analogs (e.g., BI-2536) as inhibitors of Plk1. Currently, BI-2536 is in phase II clinical trials but has high clearance (CL>1000 mL/min) and is dose limited by myelosupression in man. There is still a need for further compounds that inhibit Plk1 which possess improved potency or pharmacokinetic properties. It would also be advantageous to have a Plk1 inhibitor that could be dosed orally.

The present invention provides novel imidazolidinonyl aminopyrimidine compounds believed to have clinical use for treatment of cancer through inhibiting Plk1. Certain of these compounds are believed to have improved potency over compounds disclosed in WO 06/066172. Additionally, certain of these compounds are believed to have improved pharmacokinetic properties over BI-2536. Further, due to the oral bioavailability of the compounds of the present invention that were tested, it is believed that certain of these compounds could be dosed orally.

BRIEF SUMMARY OF THE INVENTION

The present invention provides compounds of Formula I:

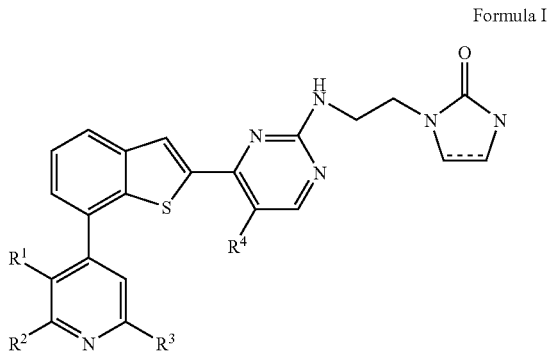

Formula I wherein:

$R^1$ is aminomethyl, ($C_1$-$C_3$ alkyl)aminomethyl, di($C_1$-$C_2$ alkyl)aminomethyl, N-ethyl-N-methyl-aminomethyl, 1-aminoethyl, 1-(($C_1$-$C_2$ alkyl)amino)-ethyl, 3,3,3-trifluoropropylaminomethyl, ethynyl, 2-hydroxy-ethoxy, 2-hydroxyethylaminomethyl, 2-cyanoethylaminomethyl, morpholin-4-ylmethyl, methoxymethoxymethyl, cyclopropyl, 1-azetidinylmethyl, 1-pyrrolidinylmethyl, or 1,3-dioxolan-2-yl;

$R^2$ is hydrogen or halo;
$R^3$ is hydrogen or halo;
provided that at least one of $R^2$ and $R^3$ is hydrogen;
$R^4$ is hydrogen, methyl, or halo; and
— is a single bond that is either present or absent, or
a pharmaceutically acceptable salt thereof.

The present invention provides a method of treating cancer selected from the group consisting of non-small cell lung, oropharyngeal, oesophageal, gastric, melanoma, epidermoid carcinoma of the skin, breast, ovarian, endometrial, colorectal, neuroglioma, glioblastoma, thyroid carcinoma, cervical, pancreatic, prostate, hepatoblastoma and non-Hodgkin lymphoma cancers in a mammal comprising administering to a mammal in need of such treatment an effective amount of a compound of Formula I or a pharmaceutically acceptable salt thereof.

The present invention also provides a pharmaceutical composition comprising a compound of Formula I or a pharmaceutically acceptable salt thereof, in combination with a pharmaceutically acceptable excipient, carrier, or diluent.

This invention also provides a compound of Formula I or a pharmaceutically acceptable salt thereof for use in the preparation of a medicament. Additionally, this invention provides a compound of Formula I or a pharmaceutically acceptable salt thereof for use in the preparation of a medicament for the treatment of cancer in mammals, selected from the group consisting of non-small cell lung, oropharyngeal, oesophageal, gastric, melanoma, epidermoid carcinoma of the skin, breast, ovarian, endometrial, colorectal, neuroglioma, glioblastoma, thyroid carcinoma, cervical, pancreatic, prostate, hepatoblastoma and non-Hodgkin lymphoma cancers. Furthermore, this invention provides a pharmaceutical composition adapted for the treatment of cancer selected from the group consisting of non-small cell lung, oropharyngeal, oesophageal, gastric, melanoma, epidermoid carcinoma of the skin, breast, ovarian, endometrial, colorectal, neuroglioma, glioblastoma, thyroid carcinoma, cervical, pancreatic, prostate, hepatoblastoma and non-Hodgkin lymphoma cancers comprising a compound of Formula I or a pharmaceutically acceptable salt thereof in combination with one or more pharmaceutically acceptable excipients, carriers, or diluents.

The present invention also provides compounds of the Formula:

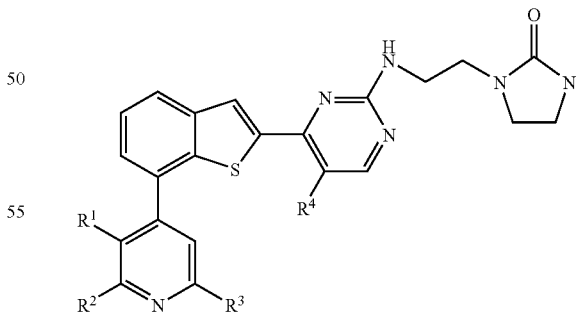

wherein:
$R^1$ is dimethylaminomethyl, morpholinylmethyl, methoxymethoxymethyl, cyclopropyl, or 1,3-dioxolan-2yl;
$R^2$ is hydrogen, or halo;
$R^3$ is hydrogen or halo;
provided that at least one of $R^2$ and $R^3$ is hydrogen;
$R^4$ is hydrogen, or halo; or
a pharmaceutically acceptable salt thereof.

DETAILED DESCRIPTION OF THE INVENTION

The general chemical terms used in the formulae above have their usual meanings. For example, the term "$C_1$-$C_3$ alkyl" means straight or branched chain alkyls such as methyl, ethyl, propyl, and isopropyl. "$C_1$-$C_2$ alkyl" is included in the meaning of "$C_1$-$C_3$ alkyl" and means methyl and ethyl. The term "halo" means fluoro, chloro, bromo, and iodo.

It will be understood by the skilled reader that most or all of the compounds of the present invention are capable of forming salts. The compounds of the present invention are amines, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol 66, No. 1, January 1977.

Preferred are compounds of Formula I wherein:

a) $R^1$ is dimethylaminomethyl;
b) $R^1$ is methylaminomethyl;
c) $R^1$ is aminomethyl;
d) $R^2$ is hydrogen;
e) $R^3$ is halo;
f) $R^3$ is fluoro;
g) $R^4$ is halo;
h) $R^4$ is fluoro;
i) $R^1$ is dimethylaminomethyl, $R^2$ is hydrogen, $R^3$ is fluoro, and $R^4$ is fluoro;
j) $R^1$ is methylaminomethyl, $R^2$ is hydrogen, $R^3$ is fluoro, and $R^4$ is fluoro; and
k) $R^1$ is aminomethyl, $R^2$ is hydrogen, $R^3$ is fluoro, and $R^4$ is fluoro.

SCHEMES

The skilled artisan will appreciate that not all of the substituents in the compounds of the present invention will tolerate certain reaction conditions employed to synthesize the compounds. These moieties may be introduced at a convenient point in the synthesis, or may be protected and then deprotected as necessary or desired. The skilled artisan will appreciate that the protecting groups may be removed at any convenient point in the synthesis of the compounds of the present invention. Methods for introducing and removing nitrogen and oxygen protecting groups are well known in the art; see, for example, Greene and Wuts, *Protective Groups in Organic Synthesis*, 3rd Ed., John Wiley and Sons, New York, Chapter 7 (1999). Furthermore, the skilled artisan will appreciate that in many circumstances, the order in which moieties are introduced is not critical. The particular order of steps required to produce the compounds of the present invention can be dependent upon the particular compound being synthesized, the starting compound, and the relative lability of the substituted moieties.

In the schemes below all substituents, unless otherwise indicated, are as previously defined and reagents are well known and appreciated in the art or exemplified in the preparations and examples.

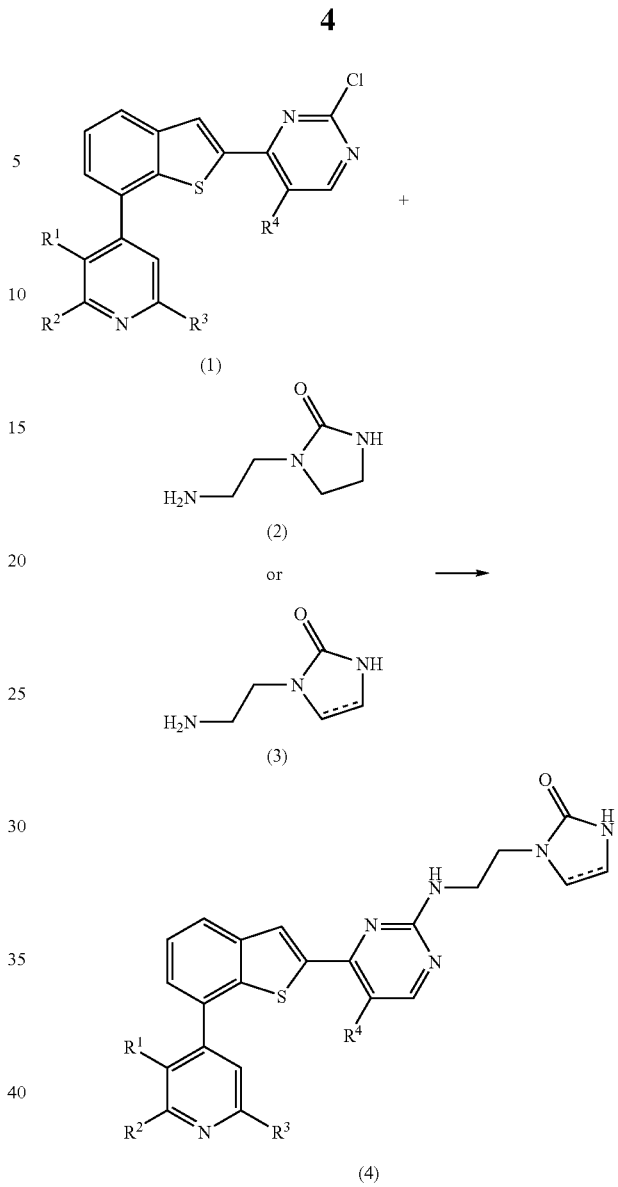

A 2-halopyrimidine compound (1) is reacted with 1-(2-aminoethyl)-2-imidazolidinone (2) or 1-(2-aminoethyl)-1,3-dihydro-2H-imidazol-2-one (3) to give compound (4) via a nucleophilic displacement reaction. Such reactions are carried out in a suitable solvent, such as n-butanol, dioxane, and the like. Generally, the reactions are carried out at temperatures of from about 120° C. to 150° C. using an oil bath or a microwave reactor. Typical stoichiometry for this reaction is about 2 equivalents of amines (2) or (3) or 1 equivalent of (2) or (3) in the presence of excess acid scavengers. such as, triethylamine or diisopropylethyl amine.

In an optional step, a pharmaceutically acceptable salt of a compound (4) is formed. The formation of such salts is well known and appreciated in the art.

As will be readily appreciated, compounds (1) can be readily prepared by methods similar to those described herein with procedures that are well-known and established in the art. For example, compound (1) is prepared by coupling an optionally substituted pyridinyl compound with an optionally substituted benzothiophenyl compound by Suzuki coupling methods. The resulting Suzuki adduct is boronylated by methods well known in the art and further coupled to an optionally substituted pyrimidine halide via Suzuki coupling methods. Also, it is recognized that the steps required to prepare compound (1) can be carried out in any order including reaction of an intermediate to compound (1) with compound (2) or (3) such that later carbon-carbon bond formation, coupling reaction, etc, provide compound (4).

The present invention is further illustrated by the following examples and preparations. These examples and preparations are illustrative only and are not intended to limit the invention in any way. The terms used in the examples and preparations have their normal meanings unless otherwise designated. The example compounds below were named using ChemDraw®, Version 10.

PREPARATIONS

Preparation 1

2-Benzo[b]thiophen-7-yl-4,4,5,5-tetramethyl-[1,3,2] dioxaborolane

Combine 7-bromo-benzo[b]thiophene (426 mg, 2 mmol), bis(pinacolato)diboron (756 mg, 3 mmol), [1,1'-bis(diphenylphosphino)ferrocene]dichloropalladium (II), complex with dichloromethane (1:1) (81 mg, 0.1 mmol), potassium acetate (294 mg, 3 mmol) in dimethyl sulfoxide (DMSO) (10 mL) in a flask. Bubble nitrogen through the mixture for 5 min. Seal the flask and put it into an oil bath and heat at 100° C. for 4 hours. Dilute the mixture with chloroform/isopropanol (3/1). Wash the solution with saturated aqueous sodium chloride. Dry the organic solution over sodium sulfate. Concentrate the solution in vacuo to a dark residue. Purify by column chromatography (hexane to 20% ethyl acetate in hexane) to afford the title compound (342 mg, 66%) as a colorless solid. MS (ES) m/z 261 [M+1]$^+$.

Preparation 2

Benzo[b]thiophene-7-boronic acid

Combine 7-bromobenzo[b]thiophene (300 g, 1.41 mmol) and triisopropylborate (403.6 g, 2.15 mmol) in anhydrous tetrahydrofuran (THF) (4000 mL) in a 12-L Morton flask fitted with a mechanical stirrer and cool under nitrogen in a dry-ice/acetone bath to −70° C. Add n-butyl lithium (1.6 M in hexane, 714 g, 1.68 mmol) dropwise at such a rate as to keep the internal temperature less than −67.5° C. After the addition is complete, allow the reaction mixture to stir at this temperature for 1 hour. Remove the cooling bath and slowly add 4 L of water. Next, add concentrated HCl (75 mL) until the pH of the solution is about pH=2. Allow the slurry to stir for 1 hour. Add sufficient 5 N aqueous NaOH to adjust the pH of the mixture to about pH=12. Separate the layers and save the aqueous layer. Dilute the organic layer with 4 L of methyl-tert-butyl ether and extract with 1 L of 5 N aqueous NaOH. Separate the layers. Combine the aqueous layer with the previous aqueous extract. Wash the aqueous layer with additional methyl-tert-butyl ether (4 L). Separate the layers and transfer the aqueous layers to a 12 L 3-neck round bottom flask fitted with a mechanical stirrer. Cool the solution to +5° C. with an ice-water bath. Add concentrated HCl slowly until the pH of the solution is about pH=2. Stir the mixture for 30 min and filter off the resulting solid. Rinse the solid on the funnel twice with 2 L of water and allow to air-dry for 30 min. Place the solid in a vacuum oven at 50° C. and dry under vacuum overnight. Remove the yellow color by slurrying the dried solid with 2 L of n-heptane for 30 min. Again filter off the solid, air-dry for 30 min, and vacuum dry at 40° C. overnight to afford the title compound (188.8 g, 75%) as a white solid. $^1$H NMR (400 MHz, CD$_3$OD) δ 7.86 (d, J=8 Hz, 1H), 7.49-7.57 (m, 2H), 7.30-7.39 (m, 2H).

Preparation 3

5-Bromomethyl-2-fluoro-4-iodo-pyridine

In a flask, combine 2-fluoro-4-iodo-picoline (10.0 g, 42.19 mmol), N-bromosuccinimide (9.76 g, 54.85 mmol), 2,2'-azobisisobutyronitrile (3.46 g, 21.10 mmol) and dry CCl$_4$ (100 mL). Heat at 70° C. under nitrogen for 16 hours. Cool to room temperature. Dilute with dichloromethane and wash with water and saturated aqueous sodium chloride. Separate the layers and dry the organic layer over magnesium sulfate. Concentrate in vacuo to give crude product. Purify by column chromatography (1% to 15% ethyl acetate in hexane) to afford the title compound (8.27 g, 62%). MS (EI) m/z 315 M$^+$.

Preparation 4

4-(6-Fluoro-4-iodo-pyridin-3-ylmethyl)-morpholine

In a flask, combine 5-bromomethyl-2-fluoro-4-iodo-pyridine (6.13 g, 19.40 mmol), morpholine (3.38 g, 38.80 mmol) and dry CH$_3$CN (100 mL) under nitrogen. Add N,N-diisopropylethylamine (6.76 mL, 38.80 mmol, 2 M THF solution). Heat at 81° C. for 2 hours and cool to room temperature. Dilute with dichloromethane and wash with water and saturated aqueous sodium chloride. Separate the organic layer from the aqueous layer and dry over magnesium sulfate. After filtration, concentrate in vacuo to give the crude title compound 6.23 g (99.7%). MS (ES) m/z 323 [M+1]$^+$.

Synthesize the following compounds using a similar procedure as for 4-(6-fluoro-4-iodo-pyridin-3-ylmethyl)-morpholine with the appropriate amine

| Prep | Compound Name | GC m/z M$^+$ | Comments |
| --- | --- | --- | --- |
| 5 | (6-Fluoro-4-iodo-pyridin-3-ylmethyl)-dimethyl-amine | 280 | dimethylamine (2 M THF solution) |
| 6 | Diethyl-(6-fluoro-4-iodo-pyridin-3-ylmethyl)-amine | 308 | diethylamine |
| 7 | (6-Fluoro-4-iodo-pyridin-3-ylmethyl)-propyl-amine | 294 | propylamine |
| 8 | Ethyl-(6-fluoro-4-iodo-pyridin-3-ylmethyl)-amine | 280 | ethylamine (2 M THF solution) |
| 9 | Ethyl-(6-fluoro-4-iodo-pyridin-3-ylmethyl)-methyl-amine | 294 | N-ethylmethyl amine |
| 10 | 2-[(6-Fluoro-4-iodo-pyridin-3-ylmethyl)-amino]-ethanol | 296 | 2-ethanol amine |
| 11 | 2-Fluoro-4-iodo-5-pyrrolidin-1-ylmethyl-pyridine | 306 | pyrrolidine |
| 12 | 5-Azetidin-1-ylmethyl-2-fluoro-4-iodo-pyridine | 292 | cyclobutyl amine |
| 13 | (6-Fluoro-4-iodo-pyridin-3-ylmethyl)-methyl-amine | 266 | Purified on normal phase silica after BOC protection |

Preparation 14

(6-Fluoro-4-iodo-pyridin-3-ylmethyl)-(3,3,3-trifluoro-propyl)-carbamic acid tert-butyl ester Add a solution of 5-bromomethyl-2-fluoro-4-iodo-pyridine (0.315 g, 997 µmol) in acetonitrile (2 mL) to a solution of 3,3,3-trifluoropropylamine hydrochloride (298 mg, 1.99 mmol) and diisopropylethylamine (521 µL, 2.99 mmol) in acetonitrile (2 mL) dropwise at room temperature. Stir the mixture overnight. Add diisopropylethylamine (522 µL, 2.99 mmoles) and di-tert-butyldicarbonate (1.088 g, 4.99 mmol) to the mixture and stir at room temperature for 6 hours. Concentrate and purify the product by column chromatography on 80 g silica gel eluting with a gradient from 1:1 hexane/dichloromethane to 50% ethyl acetate/1:1 hexane dichloromethane to give the title compound (813 mg) as a 1 to 1 mixture with (3,3,3-trifluoro-propyl)-carbamic acid tert-butyl ester. MS (ES) m/z 449 [M+1]$^+$.

Synthesize the following compound using a similar procedure as in (6-fluoro-4-iodo-pyridin-3-ylmethyl)-(3,3,3-trifluoro-propyl)-carbamic acid tert-butyl ester.

| Prep | Compound Name | GC m/z M$^+$ | comments |
|---|---|---|---|
| 15 | (2-Cyano-ethyl)-(6-fluoro-4-iodo-pyridin-3-ylmethyl)-carbamic acid tert-butyl ester | 405 | 3-amino propionitrile |

Preparation 16

[6-Fluoro-4-(4,4,5,5-tetramethyl-[1,3,2]dioxaborolan-2-yl)-pyridin-3-ylmethyl]-(3,3,3-trifluoro-propyl)-carbamic acid tert-butyl ester De-gas a suspension of (6-fluoro-4-iodo-pyridin-3-ylmethyl)-(3,3,3-trifluoro-propyl)-carbamic acid tert-butyl ester (600 mg, 1.3 mmol), potassium acetate (262.8 mg, 2.7 mmol), bis(pinacolato)diboron (407.9 mg, 1.6 mmol), and [1,1'-bis(diphenylphosphino)ferrocene]dichloropalladium(II) CH$_2$Cl$_2$ (109.2 mg, 133.9 µmol) in DMSO (5 mL). Heat the mixture at 80° C. in a sealed vessel for 4 hours. Cool the mixture to room temperature and dilute with ethyl acetate. Wash the organic solution with three portions water and one portion saturated aqueous sodium chloride, dry over sodium sulfate, filter, and evaporate. Load the crude product onto a 25 g silica gel loading column with dichloromethane and elute onto a 40 g silica gel column with a gradient from hexane to dichloromethane and then from dichloromethane to ethyl acetate to give the title compound (600 mg) as a dark oil. The product still contains (3,3,3-trifluoro-propyl)-carbamic acid tert-butyl ester from the previous step. Carry forward without further purification. GC (EI) m/z 448 M$^+$.

Preparation 17

2-Fluoro-5-methoxymethoxy-pyridine

Add 6-fluoro-pyridin-3-ol (3.5 g, 30.95 mmol) to a suspension of sodium hydride (1.49 g, 37.14 mmol) in dimethylformamide (20 mL). Stir the mixture for 1 hour. Add chloromethyl methyl ether (2 g, 25.0 mmol). Stir the mixture at room temperature overnight. Dilute the mixture with ethyl acetate and water. Wash the organic layer with water and saturated aqueous sodium chloride. Dry the mixture over sodium sulfate. Concentrate the solution in vacuo to brown oil. Purify by column chromatography (10% ethyl acetate in hexane) to afford the title compound (4.30 g, 88.4%) as yellow oil. $^1$H NMR (400 MHz, CDCl$_3$) δ 3.48 (s, 3H), 5.15 (s, 2H), 6.85 (dd, J=3.6 Hz, J=8.8 Hz, 1H), 7.47 (m, 1H), 7.96 (m, 1H).

Preparation 18

2-Fluoro-4-iodo-5-methoxymethoxy-pyridine

Cool a solution of 2-fluoro-5-methoxymethoxy-pyridine (4.1 g, 26.1 mmol) in THF (60 mL) to −75° C. Add tert-butyllithium (1.7 M in pentane, 30.4 mL, 51.66 mmol) over a period of 30 min. Stir the mixture for an additional half an hour. Add iodine (9.8 g, 38.61 mmol, dissolved in 60 mL of tetrahydrofuran). Stir for 1 hour after the addition is complete. Allow the temperature to rise to room temperature over 1 hour while stirring. Treat the mixture with water. Extract the solution with ethyl acetate three times. Wash the organic layer with saturated aqueous sodium chloride. Dry the mixture over sodium sulfate. Concentrate the solution in vacuo to a brown solid. Triturate the brown solid with hexane. Filter to afford the title compound (3.9 g, 52.8%) as a brown solid. $^1$H NMR (400 MHz, CDCl$_3$) δ 3.53 (s, 3H), 5.23 (s, 2H), 7.39 (d, J=4.0 Hz, 1H), 7.96 (d, J=1.6 Hz, 1H).

Preparation 19

6-Fluoro-4-iodo-pyridin-3-ol

Add HCl (3 M in water, 31 mL, 93.01 mmol) to a solution of 2-fluoro-4-iodo-5-methoxymethoxy-pyridine (3.9 g, 13.78 mmol) in THF (20 mL). Stir the mixture at 60° C. for 3 hours. Cool down the mixture. Adjust the pH to 7 with slow addition of saturated aqueous sodium bicarbonate solution. Extract the solution with ethyl acetate three times. Wash the organic layer with saturated aqueous sodium chloride. Dry the mixture over sodium sulfate. Concentrate the solution in vacuo to afford the title compound (3.2 g, 97.18%) as a yellow solid. MS (EI) m/z 240 [M+1]$^+$.

Preparation 20

2-Fluoro-4-iodo-5-[2-(tetrahydro-pyran-2-yloxy)-ethoxy]-pyridine

Add 6-fluoro-4-iodo-pyridin-3-ol (0.5 g, 2.09 mmol) to a suspension of sodium hydride (60% dispersion in mineral oil, 0.1 g, 2.51 mmol) in dimethylformamide (6 mL). Stir the mixture for 1 hour. Add 2-(2-bromo-ethoxy)-tetrahydro-pyran (0.51 g, 2.34 mmol). Stir the solution at room temperature overnight. Dilute the mixture with ethyl acetate and water. Wash the organic layer with saturated aqueous sodium chloride and water. Dry the mixture over sodium sulfate. Concentrate the solution in vacuo to give yellow oil. Purify the oil by column chromatography (10% ethyl acetate in hexane) to afford the title compound (0.58 g, 75.5%) as a light yellow oil. MS (EI) m/z 368 [M+1]$^+$.

Preparation 21

4-Chloro-3-trimethylsilylethynyl-pyridine

To a solution of 4-chloro-3-iodo pyridine (2.0 g, 8.3 mmol) in toluene (20 mL) add triphenyl phosphine (0.219 g, 0.83 mmol), copper iodide (0.079 g, 0.41 mmol) and palladium (II) acetate (0.093 g, 0.41 mmol), add triethylamine (3.49 mL, 25 mmol) dropwise at room temperature followed by the addition of trimethylsilylacetylene (1.65 mL, 11.69 mmol) at room temperature with continuous stirring. Stir the reaction mixture at room temperature for 2 hours. Concentrate the reaction mixture by evaporating the toluene under vacuum. Extract the compound (almost pure) by triturating with hexane and then decanting the hexane layer 4 to 5 times. Evaporate hexane under vacuum and dry it to obtain the pure compound (1.68 g, 96%). $^1$H NMR (400 MHz, CDCl$_3$) δ 8.677 (s, 1H), 8.418 (s, 1H), 7.338 (d, J=2.6 Hz, 1H), 0.286 (s, 9H). MS (ES) m/z 210 [M+1]$^+$.

Preparation 22

(6-Fluoro-4-iodo-pyridin-3-ylmethyl)-methyl-carbamic acid tert-butyl ester

Combine the crude mixture of (6-fluoro-4-iodo-pyridin-3-ylmethyl)-methyl-amine (8 g, 30.07 mmol) with diisopropylethylamine (10.49 mL, 60.14 mmol) in dry acetonitrile (50 mL) under nitrogen. Add di-tert-butyldicarbonate (13.13 g, 60.14 mmol) and stir overnight. Wash the mixture with saturated bicarbonate, water and saturated aqueous sodium chloride. Separate the organic layer from the aqueous layer and dry over MgSO$_4$. After filtration, remove the organic solvent to dryness to give a crude product. Purify the crude by column chromatography 5% to 25% ethyl acetate in hexanes to give the title compound (8.24 g, 75%). MS (ES) m/z 367 [M+1]$^+$.

Preparation 23

1-(6-Fluoro-pyridin-3-yl)-ethanol

Add methyl magnesium bromide (3 M in ether, 12 mL, 36 mmol) at 0° C. under nitrogen to a solution of 6-fluoro-pyridine-3-carbaldehyde (3 g, 24 mmol) in THF (20 mL). Continue to stir the mixture for overnight at room temperature. Hydrolyze the mixture with 1 N HCl and follow the basification with diluted ammonium hydroxide to ~pH 9. Abstract the product with chloroform/isopropyl alcohol (3/1). Dry over sodium sulfate. Concentrate the solution in vacuo to yellow oil. Purify by column chromatography (10% methanol in dichloromethane) to give the product as a colorless oil (2.3 g, 68%). MS (ES) m/z 142 [M+1]$^+$.

Preparation 24

2-Fluoro-5-(1-methoxymethoxy-ethyl)-pyridine

Add N,N'-diisopropylethylamine and chloromethoxymethane to a solution of 1-(6-fluoro-pyridin-3-yl)-ethanol (3.0 g, 21.3 mmol) in dichloromethane at 0° C. Continue to stir the mixture for 30 min at 0° C., then overnight at room temperature. Dilute the mixture with chloroform/isopropyl alcohol (3/1). Wash the solution with saturated aqueous sodium chloride. Dry it over sodium sulfate. Concentrate the solution in vacuo to a dark residue. Purify by column chromatography (hexane→20% ethyl acetate in hexane) to afford the product as a colorless solid (3 g, 66%). MS (ES) m/z 186 [M+1]$^+$.

Preparation 25

5-Azidomethyl-2-fluoro-4-iodo-pyridine

Combine 5-bromomethyl-2-fluoro-4-iodo-pyridine (0.45 g, 1.4 mmol), sodium azide (370 mg, 5.7 mmol), and 18-crown ether (45 mg, 0.17 mml) in dimethylformamide (10 mL) in a round bottom flask. Stir the mixture for 4 hours at room temperature. Dilute the reaction mixture with chloroform, and wash with water and saturated aqueous sodium chloride. Separate the organic layer from the aqueous layer and dry over MgSO$_4$. After filtration, evaporate the organic solvent in vacuo to give a crude product. Purify the crude with flash column chromatography (eluted with 20% methyl acetate in hexane) to give the title compound (colorless oil, 0.0.32 g, 82%). MS (ES) m/z 279 [M+1]$^+$ Preparation 26

(4-Chloro-pyridin-3-yl)-morpholin-4-yl-methanone

Combine 4-chloronicotinic acid (0.10 g, 6.0 mmol) and 1,1'-carbonyldiimidazole (0.97 g, 6.0 mmol) in dry THF (15 mL). Stir at room temperature under nitrogen for 90 min. Add morpholine (1.58 mL, 18.0 mmol) and stir at room temperature under nitrogen for 15 hours. Dilute with dichloromethane, wash with saturated aqueous sodium hydrogen carbonate solution, and saturated aqueous sodium chloride. Separate the layers and dry the organic layer over magnesium sulfate. Concentrate in vacuo. Purify the crude residue by column chromatography [5% to 25% (10% 2 M ammonia/methanol solution in dichloromethane)/dichloromethane] to give the title compound (1.17 g, 86%). MS (ES) m/z 227 [M+1]$^+$.

Preparation 27

4-(4-Chloro-pyridin-3-ylmethyl)-morpholine

Dissolve (4-chloro-pyridin-3-yl)-morpholin-4-yl-methanone (1.17 g, 5.17 mmol) in dry THF (10 mL). Add a solution of 2 M BH$_3$—Me$_2$S/THF (15 mL, 31.0 mmol) dropwise at room temperature under nitrogen. Stir at room temperature for 15 hours under nitrogen. Add methanol (11.0 mL) very slowly dropwise. Heat at 60° C. for 3 hours, and cool to room temperature in vacuo to afford the title compound (1.1 g, 100%). MS (ES) m/z 213 [M+1]$^+$.

Preparation 28

5-[1,3]Dioxolan-2-yl-2-fluoro-pyridine

In a pressure vessel, combine 6-fluoro-pyridine-3-carbaldehyde (4 g, 32 mmol), ethylene glycol (3 g, 48 mmol), copper (II) chloride di-hydrate (0.56 g, 3.2 mmol) and THF (10 mL). Heat the mixture at 100° C. for 1 hour. Dilute the mixture with chloroform-isopropanol (3:1, 100 mL). Wash the organic phase with saturated aqueous sodium chloride and water. Dry the organic layer over sodium sulfate. Concentrate the solution in vacuo to brown oil. Purify by column chromatography (20% ethyl acetate in hexane) to afford the title compound (2.1 g, 39%) as a pale yellow oil. MS (ES) m/z 170 [M+1]$^+$.

Preparation 29

5-[1,3]Dioxolan-2-yl-2-fluoro-3-iodo-pyridine

Cool a solution of 5-[1,3]dioxolan-2-yl-2-fluoro-pyridine (2.0 g, 11.8 mmol) in THF (20 mL) to −75° C. Add lithium diisopropylamide (2 M in THF, 6 mL, 12 mmol) over a period of 30 min. Stir the mixture for an additional 3 hours. Add iodine (3.0 g, 11.8 mmol, dissolved in 100 mL of THF). Stir for 2 hours after the addition is complete. Add water (100 mL) to the mixture and allow the temperature to rise to room temperature over 1 hour while stirring. Treat the mixture with saturated aqueous sodium thiosulfate solution (50 mL). Extract the solution with ether. Concentrate the solution in vacuo to a brown oil. Purify by column chromatography (hexane to 20% ethyl acetate in hexane) to afford the title compound (2.1 g, 60%) as a yellow oil. MS (ES) m/z 296 [M+1]$^+$.

Synthesize the following compounds using a similar procedure as for 5-[1,3]dioxolan-2-yl-2-fluoro-3-iodo-pyridine.

| Prep | Compound Name | MS (ES) [M + 1]$^+$ |
|---|---|---|
| 30 | 2-Fluoro-3-iodo-5-(1-methoxymethoxy-ethyl)-pyridine | 312 |

Preparation 31

5-[1,3]Dioxolan-2-yl-2-fluoro-4-iodo-pyridine

Cool a solution of 5-[1,3]dioxolan-2-yl-2-fluoro-3-iodo-pyridine (2.0 g, 6.8 mmol) in THF (20 mL) to −75° C. Add lithium diisopropylamide (2 M in THF, 3.4 mL, 6.8 mmol) over a period of 30 min. Stir the mixture for an additional 3 hours. Add water (100 mL) and allow the temperature to rise to room temperature over 1 hour while stirring. Extract the solution with ether. Concentrate the solution in vacuo to a brown oil. Purify by column chromatography (hexane to 15% ethyl acetate in hexane) to afford the title compound (1.03 g, 51%) as a yellow oil. MS (ES) m/z 296 [M+1]$^+$.

Synthesize the following compounds using a similar procedure as for 5-[1,3]dioxolan-2-yl-2-fluoro-4-iodo-pyridine.

| Prep | Compound Name | MS (ES) [M + 1]$^+$ |
|---|---|---|
| 32 | 2-Fluoro-4-iodo-5-(1-methoxymethoxy-ethyl)-pyridine | 312 |

Preparation 33

1-(6-Fluoro-4-iodo-pyridin-3-yl)-ethanol

Add 1 N HCl (5 mL) to a solution of 2-fluoro-4-iodo-5-(1-methoxymethoxy-ethyl)-pyridine (1 g, 3.2 mmol) in methanol (10 mL). Stir the mixture overnight. Dilute the reaction mixture with 2 N sodium carbonate. Abstract the product into chloroform. Dry the organic phase over sodium sulfate. Concentrate the solution in vacuo to a give the crude. Purify the crude by column chromatography (10% methanol in dichloromethane) to afford the product as a white solid (0.75 g, 87%). MS (ES) m/z 268 [M+1]$^+$.

Preparation 34

5-(1-Azido-ethyl)-2-fluoro-4-iodo-pyridine

Add tetra-N-butylammonium azide to a solution of triphenylphine (11 g, 42 mmol) and 1,4-cyclohexadiene-2,2-dicarbonitrile,4,5-dichloro-3,6-dioxo-(9 g, 40 mmol) in dichloromethane (150 mL) under ice-bath cooling. Then add 1-(6-fluoro-4-iodo-pyridin-3-yl)-ethanol (6.7 g, 25.1 mmol) to the above solution. Stir the mixture at room temperature for 1 hour. Concentrate the mixture in vacuo to about 50 mL. Purify the residue by flash column chromatography (hexane to 20% ethyl acetate in hexane as gradient) to give target product as colorless oil (5.7 g, 78%). MS (ES) m/z 293 [M+1]$^+$.

Preparation 35

R-5-(1-Azido-ethyl)-2-fluoro-4-iodo-pyridine

Separate 5-(1-azido-ethyl)-2-fluoro-4-iodo-pyridine (11.7 g) by chiral chromatography (Chiralpak® AS-H column, 15:85:isopropyl alcohol/C7 at 270 nm) to give R-1-(1-azido-ethyl)-4-fluoro-2-iodo-benzene (3.82 g, 33%).

Preparation 36

1-(6-Chloro-pyridin-3-yl)-ethylamine

Stir a mixture of 1-(6-chloro-pyridin-3-yl)-ethanone (5 g, 32.14 mmol) in titanium tetra(isopropoxide) (18.27 g, 64.27 mmol) and ammonia (160.7 mmol, 2 M in MeOH) under $N_2$ for 6 hours at room temperature. To this mixture add sodium tetrahydroborate (1.82 g, 48.21 mmol) and stir overnight. Quench the reaction mixture with ammonium hydroxide and filter the mixture. From the filtrate remove the solvent and extract the residue with dichloromethane, wash with saturated aqueous sodium chloride and dry over $Na_2SO_4$, filter and remove the solvent to obtain a dark yellow oil (4.2 g). MS (ES) m/z 157 [M+1]$^+$.

Preparation 37

[1-(6-Chloro-pyridin-3-yl)-ethyl]-carbamic acid tert-butyl ester

To a solution of 1-(6-chloro-pyridin-3-yl)-ethylamine (4.2 g, 26.82 mmol) in acetonitrile (50 mL) add diisopropylethylamine (5.2 g, 40.23 mmol) and di-tert-butyldicarbonate (7.02 g, 32.18 mmol) and stir the mixture overnight. Wash the mixture with saturated $NaHCO_3$ (200 mL) and extract in dichloromethane, wash with saturated aqueous sodium chloride and dry over $Na_2SO_4$. Purify by column chromatography 5% to 20% ethyl acetate in hexanes to obtain a white solid (5.1 g). MS (ES) m/z 257 [M+1]$^+$.

Preparation 38

[1-(6-Chloro-4-iodo-pyridin-3-yl)-ethyl]-carbamic acid tert-butyl ester

Add tert-butyllithium (35 mL, 59.6 mmol) to a solution of [1-(6-chloro-pyridin-3-yl)-ethyl]-carbamic acid tert-butyl ester (5.1 g, 19.87 mmol) in THF (60 mL) under $N_2$ at −78° C. After 30 min, add iodine (7.6 g, 29.8 mmol) in THF (20 mL) over 30 min at −78° C. Stir for 1 hour and then warm up to room temperature. Quench with water, extract in ethyl acetate with saturated aqueous sodium chloride, dry over $Na_2SO_4$. Purify on column chromatography 5% to 20% ethyl acetate in hexanes to obtain product (1 g). MS (ES) m/z 383 [M+1]$^+$.

Preparation 39

5-(1-Azido-ethyl)-2-fluoro-pyridine

To a 1-L flask kept cold in a ice bath, add triphenylphosphine (27.9 g, 106.3 mmol), 1,4-cyclohexadiene-1,2-dicarbonitrile, 4,5-dichloro-3,6-dioxo-(24.12 g, 106.3 mmol). Add dichloromethane slowly with stirring (150 mL). To the dark solution add tetra-N-butylammonium azide (30.23 g, 106.3 mmol) slowly, followed by 1-(6-fluoro-pyridin-3-yl)-ethanol (10 g, 70.85 mmol) dissolved in dichloromethane (10 mL). Remove the flask from the ice bath and stir at room temperature for 1 hour. Remove the solvent on a rotovap and purify by normal phase chromatography 5% to 20% ethyl acetate in hexanes to obtain the product as colorless oil (7.75 g). GCMS (EI) m/z 166 M+.

Preparation 40

1-(6-Fluoro-pyridin-3-yl)-ethylamine

Hydrogenate 5-(1-azido-ethyl)-2-fluoro-pyridine (4.09 g, 24.59 mmol) under a 60 psi pressure in ethanol (200 mL) in presence of $PtO_2$ (6% w/w). Filter the mixture after 4 hours, remove the solvent on a rotovap, and dry the resulting oil under vacuum to obtain the product (3.149 g). GCMS (EI) m/z 140 M+.

Preparation 41

[1-(6-Fluoro-pyridin-3-yl)-ethyl]-carbamic acid tert-butyl ester

To a solution of 1-(6-fluoro-pyridin-3-yl)-ethylamine (14.86 g, 106.01 mmol) in acetonitrile (100 mL) add diisopropylethylamine (37 mL, 212 mmol) and di-tert-butyldicarbonate (46.27 g, 212 mmol). Stir the mixture overnight. Wash with saturated $NaHCO_3$, extract in dichloromethane, wash with saturated aqueous sodium chloride, dry over $Na_2SO_4$. Purify on column chromatography 10% to 70% ethyl acetate in hexanes to obtain product as white solid (20 g). MS (ES) m/z 241 [M+1]+.

Preparation 42

[1-(6-Fluoro-4-iodo-pyridin-3-yl)-ethyl]-carbamic acid tert-butyl ester

Add a solution of [1-(6-fluoro-pyridin-3-yl)-ethyl]-carbamic acid tert-butyl ester (9.3 g, 38.8 mmol) in dry THF (90 mL) into tert-butyllithium (68.4 mL, 116.3 mmol, 1.7 M solution in pentane) in dry THF (70 mL) over 15 min under $N_2$ at −78° C. Stir at −78° C. for 1 hour. Add a solution of iodine (14.8 g, 58.2 mmol) in dry THF (90 mL) over 15 min. Stir at −78° C. for 2 hours. Warm up to 0° C. Add water. Warm up to room temperature. Extract with ethyl acetate. Wash the organic layer with $Na_2CO_3$ solution, water and saturated aqueous sodium chloride, and dry over $MgSO_4$. After filtration, concentrate and purify the crude by flash chromatography (5% to 20% ethyl acetate/hexane). Afford the desired product [1-(6-fluoro-4-iodo-pyridin-3-yl)-ethyl]-carbamic acid tert-butyl ester (2.8 g, 20%), MS (ES) m/z 367 [M+1]+.

Preparation 43

Ethyl-[1-(6-fluoro-4-iodo-pyridin-3-yl)-ethyl]-carbamic acid tert-butyl ester

Add sodium hydride (84.0 mg, 2.1 mmol, 60% dispersion in mineral oil) to a solution of [1-(6-fluoro-4-iodo-pyridin-3-yl)-ethyl]-carbamic acid tert-butyl ester (0.37 g, 1.0 mmol) in dimethylformamide (10 mL). Stir at room temperature for 30 min. Add iodoethane (0.2 mL, 2.1 mmol). Stir for 1 hour. Quench the reaction with water. Extract with $CH_2Cl_2$. Wash the organic layer with water and saturated aqueous sodium chloride. Dry over $MgSO_4$. After filtration, afford crude product ethyl-[1-(6-fluoro-4-iodo-pyridin-3-yl)-ethyl]-carbamic acid tert-butyl ester (0.4 g, 97%) with 90% HPLC purity, MS (ES) m/z 395 [M+1]+.

Prepare the following compound with procedures similar to ethyl-[1-(6-fluoro-4-iodo-pyridin-3-yl)-ethyl]-carbamic acid tert-butyl ester.

| Prep | Compound Name | MS (ES) [M + 1]+ |
|---|---|---|
| 44 | 1-(6-Fluoro-4-iodo-pyridin-3-yl)-ethyl]-methyl-carbamic acid tert-butyl ester | 381 |

Preparation 45

2-Fluoro-4-iodo-3-methoxymethoxymethyl-pyridine

Add chloromethyl methyl ether (2 g, 25.0 mmol) gradually to a solution of 2-fluoro-4-iodo-pyridin-3-yl)-methanol (1.0 g, 3.95 mmol) and N,N-diisopropylethylamine (5 g, 39 mmol) in dichloromethane (5 mL). Stir the mixture at room temperature overnight. Dilute the mixture with chloroform. Wash the organic layer with saturated aqueous sodium chloride and water. Dry the mixture over sodium sulfate. Concentrate the solution in vacuo to a brown oil. Purify by column chromatography (10% methanol in dichloromethane) to afford the title compound (0.90 g, 77%) as yellow oil. MS (ES) m/z 298 [M+1]+.

Preparation 46

5-Cyclopropyl-2-fluoro-pyridine

In a flask, combine 2-fluoro-5-iodo-pyridine (1.12 g, 5 mmol), cyclopropylboronic acid (645 mg, 7.5 mmol), palladium acetate (56 mg, 0.25 mmol), potassium phosphate (3.2 g, 15 mmol), and toluene-water (20:1, 21 mL). Heat the mixture at 100° C. for 4 hours. Dilute the mixture with chloroform-isopropanol (3:1, 100 mL). Wash the organic phase with saturated aqueous sodium chloride and water. Dry the mixture over sodium sulfate. Concentrate the solution in vacuo to a brown oil. Purify by column chromatography (20% ethyl acetate in hexane) to afford the title compound (430 mg, 63%) as a pale yellow oil. $^1H$ NMR (400 MHz-$CDCl_3$) δ 7.99 (d, J=3 Hz, 1H), 7.39 (td, J=3, 5 Hz, 1H), 6.79 (dd, J=3, 8 Hz, 1H), 0.96-1.02 (m, 2H), 0.63-0.69 (m, 2H).

Preparation 47

5-Cyclopropyl-2-fluoro-3-iodo-pyridine

Cool a solution of 5-cyclopropyl-2-fluoro-pyridine (1.3 g, 9.5 mmol) in THF (20 mL) to −75° C. in a dry ice-acetone bath under nitrogen. Add lithium diisopropylamide (2 M in THF, 6 mL, 12 mmol) over a period of 30 min. Stir the mixture for an additional 3 hours. Add iodine (2.9 g, 11.4 mmol, dissolved in 50 mL of THF) and stir the mixture for 2 hours. Add water (100 mL) and allow the temperature to rise to room temperature over 1 hour while stirring. Treat the mixture with saturated aqueous sodium thiosulfate solution (50 mL). Extract the solution with ether. Concentrate the solution in vacuo to brown oil. Purify by column chromatography (hexane to 20% ethyl acetate in hexane) to afford the title compound (1.7 g, 68%) as a yellow oil. $^1$H NMR (400 MHz-CDCl$_3$) δ 8.03 (dd, J=3, 8 Hz, 1H), 7.99 (s, 1H), 0.91-1.00 (m, 2H), 0.71-0.78 (m, 2H).

Preparation 48

5-Cyclopropyl-2-fluoro-4-iodo-pyridine

Cool a solution of 5-cyclopropyl-2-fluoro-3-iodo-pyridine (1.7 g, 6.5 mmol) in THF (20 mL) to −75° C. in dry ice-acetone bath under nitrogen. Add lithium diisopropylamide (2 M in THF, 3.9 mL, 7.8 mmol) during a period of 30 min. Stir the mixture for another 3 hours before adding water (100 mL). Then allow the temperature to rise to room temperature during 1 hour under stirring. Extract the solution with ether. Concentrate the solution in vacuo to brown oil. Purify the oil by column chromatography (hexane→15% ethyl acetate in hexane) to afford the product as a yellow oil (1.1 g, 65%).

Preparation 49

4-(4-Benzo[b]thiophen-7-yl-6-fluoro-pyridin-3-ylmethyl)-morpholine

Combine 4-(6-fluoro-4-iodo-pyridin-3-ylmethyl)-morpholine (0.48 g, 1.5 mmol), 2-benzo[b]thiophen-7-yl-4,4,5,5-tetramethyl-[1,3,2]dioxaborolane (0.47 g, 1.8 mmol) and sodium carbonate (0.39 g, 3.75 mmol) in CH$_3$CN (8 mL) and water (4 mL). Purge the mixture with nitrogen for 5 min. Add [1,1'-bis(diphenylphosphino)ferrocene]dichloropalladium (II), complex with dichloromethane (1:1) (5.0 mg, 0.6 mmol) and purge with nitrogen for an additional 5 min. Heat the mixture at 120° C. for 10 min in microwave reactor and cool to room temperature. Dilute the reaction mixture with ethyl acetate, wash with water and saturated aqueous sodium chloride. Separate the organic layer and dry over magnesium sulfate. Filter and concentrate in vacuo to give a crude mixture. Purify by column chromatography (0.1% to 1% 2 M ammonia in methanol/dichloromethane) to afford the title compound (0.43 g, 87%). MS (ES) m/z 329 [M+1]$^+$.

Prepare the following compounds using the procedure of 4-(4-benzo[b]thiophen-7-yl-6-fluoro-pyridin-3-ylmethyl)-morpholine using the appropriate starting material.

| Prep | Compound Name | Physical Data MS (ES) m/z [M + 1]$^+$ |
|---|---|---|
| 50 | 1-(2-{4-[7-(5-Dimethylaminomethyl-2-fluoro-pyridin-4-yl)-benzo[b]thiophen-2-yl]-5-fluoro-pyrimidin-2-ylamino}-ethyl)imidazolidin-2-one; compound with methane | 287 |
| 51 | 4-(4-Benzo[b]thiophen-7-yl-pyridin-3-ylmethyl)-morpholine | 311 |
| 52 | 4-Benzo[b]thiophen-7-yl-5-[1,3]dioxolan-2-yl-2-fluoro-pyridine | 302 |
| 53 | 4-Benzo[b]thiophen-7-yl-2-fluoro-3-methoxymethoxy-methyl-pyridine | 304 |
| 54 | 4-Benzo[b]thiophen-7-yl-5-cyclopropyl-2-fluoro-pyridine | 270 |
| 55 | (4-Benzo[b]thiophen-7-yl-6-fluoro-pyridin-3-ylmethyl)-methyl-carbamic acid tert-butyl ester | 373 |
| 56 | R-5-(1-Azido-ethyl)-4-benzo[b]thiophen-7-yl-2-fluoro-pyridine | 299 |

Preparation 57

1-(4-Benzo[b]thiophen-7-yl-6-fluoro-pyridin-3-yl)-ethylamine

To a solution of R-5-(1-azido-ethyl)-4-benzo[b]thiophen-7-yl-2-fluoro-pyridine (580 mg, 1.9 mmol) in ethanol (10 mL) in a round bottom flask add hydrazine formic acid salt (1:1) and 0.5 g of Raney Nickel. Stir the mixture for 3 hours at room temperature. Pour the reaction mixture diluted sodium carbonate solution. Abstract the product into chloroform, and wash with water and saturated aqueous sodium chloride. Separate the organic layer from the aqueous layer and dry over Na$_2$SO$_4$. After filtration, evaporate the organic solvent in vacuo to give the desired product as yellow solid (530 mg, 100%). MS (ES) m/z 273 [M+1]$^+$.

Preparation 58

[1-(4-Benzo[b]thiophen-7-yl-6-fluoro-pyridin-3-yl)-ethyl]-carbamic acid tert-butyl ester To a solution of 1-(4-benzo[b]thiophen-7-yl-6-fluoro-pyridin-3-yl)-ethylamine (530 mg, 1.9 mmol) in dioxane (30 mL) and water (10 mL) in a round bottom flask add di-tert-butyldicarbonate (647 mg, 2.9 mmol). Stir the mixture for 2 hours at room temperature. Pour the reaction mixture into chloroform, and wash with water and saturated aqueous sodium chloride. Separate the organic layer from the aqueous layer and dry over Na$_2$SO$_4$. After filtration, evaporate the organic solvent in vacuo to give the crude. Purify the crude by flash chromatography (hexane to 20% ethyl acetate in hexane) to give the desired product as a white solid (550 mg, 76%). MS (ES) m/z 373 [M+1]$^+$.

Preparation 59

4-Benzo[b]thiophen-7-trimethylsilylethynyl-1-pyridine

Add 4-chloro-3-trimethylsilylethynyl-pyridine (1.0 g, 4.78 mmol) to a solution of THF:H$_2$O, add potassium carbonate (1.97 g, 14.3 mmol) and 2-benzo[b]thiophen-7-yl-4,4,5,5-tetramethyl-[1,3,2]dioxaborolane (1.49 g, 5.72 mmol). Degas the reaction mixture for 30 min. Add Pd catalyst (0.218 g, 0.2 mmol) and tri(tert-butyl phosphino) tetrafluoro borate (0.120 g, 0.4 mmol) under N$_2$ atmosphere. Heat the reaction mixture at 80° C. for 2 hours. Evaporate all THF under vacuum, dilute the reaction mixture with ethyl acetate and wash with saturated aqueous sodium chloride, extract the organic layer and dry over Na$_2$SO$_4$ Filter and concentrate under vacuum, pass the crude through silica gel (60-120 mesh) column to have pure compound. Yield (0.7 g, 48%), MS (ES) m/z 308 [M+1]$^+$.

Preparation 60

4-{4-[2-(2-Chloro-pyrimidin-4-yl)-benzo[b]thiophen-7-yl]-6-fluoro-pyridin-3-ylmethyl}-morpholine Solution A: Combine 4-(4-benzo[b]thiophen-7-yl-6-fluoro-pyridin-3-ylmethyl)-morpholine (0.43 g, 1.31 mmol) and triisopropylborate (0.43 g, 2.63 mmol) in dry THF (5 mL) at −78° C. under nitrogen. Add 1.5 M lithium diisopropylamide mono(THF) in cyclohexane (2.2 mL, 3.28 mmol) under nitrogen. Stir under nitrogen at −78° C. for 1 hour and warm the reaction to room temperature.

Solution B: Combine 2,4-dichloropyrimidine (0.29 g, 1.97 mmol), 2-(di-tert-butylphospho)biphenyl (0.01 g, 0.04 mmol) and sodium carbonate (0.42 g, 3.94 mmol) in THF (7 mL) and water (3 mL). Purge with nitrogen for 5 min. Add [1,1'-bis(diphenylphosphino)ferrocene]dichloropalladium (II), complex with dichloromethane (1:1) (0.05 g, 0.07 mmol). Heat the mixture at 60° C. under nitrogen.

Add solution A to solution B dropwise through a syringe over 20 min. Heat the reaction mixture for 1 hour at 60° C. under nitrogen and cool to room temperature. Dilute the reaction mixture with ethyl acetate, wash with water and saturated aqueous sodium chloride. Separate the organic layer and dry over magnesium sulfate. Filter and concentrate in vacuo to give the crude product. Purify by column chromatography [0.1% to 1% 2 M ammonia in methanol/dichloromethane] to afford the title compound (0.42 g, 73%). MS (ES) m/z 441 [M+1]$^+$.

Prepare the following compounds essentially according to the preparation of 4-{4-[2-(2-chloro-pyrimidin-4-yl)-benzo[b]thiophen-7-yl]-6-fluoro-pyridin-3-ylmethyl}-morpholine using the appropriate starting material.

| Prep | Compound Name | MS (ES) m/z [M + 1]$^+$ |
|---|---|---|
| 61 | {4-[2-(2-Chloro-5-fluoro-pyrimidin-4-yl)-benzo[b]thiophen-7-yl]-6-fluoro-pyridin-3-ylmethyl}-dimethyl-amine | 417 |
| 62 | 4-{4-[2-(2-Chloro-5-fluoro-pyrimidin-4-yl)-benzo[b]thiophen-7-yl]-6-fluoro-pyridin-3-ylmethyl}-morpholine | 459 |
| 63 | {4-[2-(2-Chloro-pyrimidin-4-yl)-benzo[b]thiophen-7-yl]-6-fluoro-pyridin-3-ylmethyl}-dimethyl-amine | 399 |
| 64 | 4-{4-[2-(2-Chloro-5-fluoro-pyrimidin-4-yl)-benzo[b]thiophen-7-yl]-pyridin-3-ylmethyl}-morpholine | 441 |
| 65 | 2-Chloro-4-[7-(2-fluoro-5-methyl-pyridin-4-yl)-benzo[b]thiophen-2-yl]-pyrimidine | 432 |
| 66 | 2-Chloro-5-fluoro-4-[7-(2-fluoro-3-methoxymethoxy-methyl-pyridin-4-yl)-benzo[b]thiophen-2-yl]-pyrimidine | 434 |
| 67 | 2-Chloro-4-[7-(2-cyclopropyl-5-fluoro-phenyl)-benzo[b]thiophen-2-yl]-5-fluoro-pyrimidine | 400 |
| 68 | (1-{4-[2-(2-Chloro-5-fluoro-pyrimidin-4-yl)-benzo[b]thiophen-7-yl]-6-fluoro-pyridin-3-yl}-ethyl)-carbamic acid tert-butyl ester | 503 |
| 69 | {4-[2-(2-Chloro-5-fluoro-pyrimidin-4-yl)-benzo[b]thiophen-7-yl]-6-fluoro-pyridin-3-ylmethyl}-methyl-carbamic acid tert-butyl ester | 503 |
| 70 | {4-[2-(2-Chloro-5-methyl-pyrimidin-4-yl)-benzo[b]thiophen-7-yl]-6-fluoro-pyridin-3-ylmethyl}-methyl-carbamic acid tert-butyl ester | 500 |
| 71 | 4-(7-Bromo-benzo[b]thiophen-2-yl)-2-chloro-5-fluoro-pyrimidine | 476 |
| 72 | 4-(7-Bromo-benzo[b]thiophen-2-yl)-2-chloro-5-chloro-pyrimidine | 361 |
| 73 | 4-(7-Bromo-benzo[b]thiophen-2-yl)-2-chloro-5-methyl-pyrimidine | 340 GCMS (EI) M$^+$ |
| 74 | 4-(7-Bromo-benzo[b]thiophen-2-yl)-2-chloro-pyrimidine | 327 |

Preparation 75

(2-Azidocarbonyl-ethyl)-carbamic acid tert-butyl ester

Add ethyl chloroformate (2.52 g, 23.25 mmol) dropwise to a solution of 3-tert-butoxycarbonylamino-propionic acid (4 g, 21.14 mmol) and 4-methyl morpholine (2.35 g, 23.25 mmol) in THF (60 mL) at −20° C. After 40 min, warm the suspension to −5° C. and add dropwise a solution of sodium azide (3.44 g, 52.85 mmol) in water (10 mL). After 10 min, dilute the mixture with ethyl acetate (60 mL) and wash with water, saturated aqueous sodium chloride, dry over MgSO$_4$. After filtration, remove the organic solvent to afford the product as clear oil (4.3 g, 95%). $^1$H NMR (DMSO-d$_6$) δ 6.91 (broad s, 1H), 3.18 (q, J=6.4 Hz, 2H), 2.51-2.48 (m, 2H), 1.37 (s, 9H).

Preparation 76

(2-Isocyanato-ethyl)-carbamic acid tert-butyl ester

Stir a solution of (2-azidocarbonyl-ethyl)-carbamic acid tert-butyl ester (4.3 g, 20.07 mmol) in toluene (50 mL) at 65° C. for 25 minutes until the evolution of N$_2$ gas stops. Cool the solution. $^1$H NMR (DMSO-d$_6$) δ 7.06 (broad s, 1H), 3.33-3.29 (m, 2H), 3.12 (q, J=5.8 Hz, 2H), 1.39 (s, 9H).

Preparation 77

{2-[3-(2,2-Diethoxy-ethyl)-ureido]-ethyl}-carbamic acid tert-butyl ester

Add 2,2-diethoxy ethanamine (3.33 g, 25.04 mmol) to a solution of (2-isocyanato-ethyl)-carbamic acid tert-butyl ester (3.73 g, 20.03 mmol) in toluene (50 mL). After 1 hour, concentrate the mixture to afford a white solid (6.39 g). $^1$H NMR (DMSO-d$_6$) δ 6.74 (t, J=5 Hz, 1H), 6.03 (t, J=5.6 Hz, 1H), 5.85 (t, J=5.8 Hz, 1H), 4.39 (t, J=5.4 Hz, 1H), 3.61-3.55 (m, 2H), 3.48-3.42 (m, 2H), 3.06 (t, J=5.7 Hz, 2H), 3.01 (q, J=6.2 Hz, 2H), 2.92 (q, J=6.2 Hz, 2H), 1.37 (s, 9H), 1.11 (t, J=6.4 Hz, 6H).

Preparation 78

[2-(2-Oxo-2,3-dihydro-imidazol-1-yl)-ethyl]-carbamic acid tert-butyl ester

Dissolve {2-[3-(2,2-diethoxy-ethyl)-ureido]-ethyl}-carbamic acid tert-butyl ester (6.5 g, 20.35 mmol) in methanol (75 mL) and water (40 mL). To the reaction mixture add HCl (0.4 N, 50 mL) dropwise over 30 min. Stir the mixture overnight and neutralize by adding KOH (0.4 M, 50 mL), and concentrate in vacuo. Extract the residue in chloroform and wash with saturated aqueous sodium chloride, dry over MgSO$_4$, filter and remove solvent on a rotovap to give a crude white solid. Purify by column chromatography 1% to 10% MeOH in dichloromethane to afford the pure product as a white solid (2.53 g, 11.13 mmol). GCMS (EI) m/z 227 M$^+$.

Preparation 79

1-(2-Amino-ethyl)-1,3-dihydro-imidazol-2-one; compound with trifluoro-acetic acid Add trifluoro-acetic acid (10 mL) to a solution of [2-(2-oxo-2,3-dihydro-imidazol-1-yl)-ethyl]-carbamic acid tert-butyl ester (2.5 g, 11 mmol) in dichloromethane (10 mL). Stir the mixture for 3 hours. Remove most of the solvent and trifluoro-acetic acid on a rotovap and dry the yellowish thick oil under vacuum to get the product. GCMS (EI) m/z 127 M+.

Preparation 80

{1-[6-Fluoro-4-(2-{5-fluoro-2-[2-(2-oxo-2,3-dihydro-imidazol-1-yl)-ethylamino]-pyrimidin-4-yl}-benzo[b]thiophen-7-yl)-pyridin-3-yl]-ethyl}-carbamic acid tert-butyl ester Combine (1-{4-[2-(2-chloro-5-fluoro-pyrimidin-4-yl)-benzo[b]thiophen-7-yl]-6-fluoro-pyridin-3-yl}-ethyl)-carbamic acid tert-butyl ester (150 mg, 0.3 mmol), 1-(2-aminoethyl)-1,3-dihydro-imidazol-2-one (70 mg, 0.55 mmol) and triethylamine (80 mg, 0.8 mmol) in N-methylpyrrolidone (1.0 mL) in a pressure tube. Heat the reaction mixture at 130° C. for 1 hour in a microwave reactor and then cool to room temperature. Dilute the reaction mixture with ethyl acetate, and wash with water and saturated aqueous sodium chloride. Separate the organic layer from the aqueous layer and dry over MgSO4. After filtration, evaporate the organic solvent to give the crude. Purify the crude by column chromatography (10% methanol in dichloromethane) to afford the desired product (80 mg, 74%). MS (ES) m/z 538 [M+t-Bu]+, 494 [M-Boc]−, 616 [M+Na]+.

Preparation 81

2-Chloro-4-[7-(3-trimethylsilanylethynyl-pyridin-4-yl)-benzo[b]-thiophen-2-yl]-pyrimidine Add 2,4-dichloro pyrimidine (0.29 g, 1 mmol) and sodium carbonate (2.0 M, 0.273 g, 2.6 mmol) to the solution of THF in a round bottom flask. De-gas the reaction mixture for 30 min and add the Pd catalyst (0.053 g, 0.06 mmol) and then reflux the reaction mixture for 1.5 hours. Simultaneously in another round bottom flask add 4-benzo[b]thiophen-7-trimethylsilylethynyl-1-pyridine (0.40 g, 1.3 mmol) under N2 atmosphere, add tris-isopropyl borate (0.59 mL, 2.5 mmol) at room temperature. Add lithium diisopropylamide (1.9 mL, 3.8 mmol) at −78° C. drop wise. Stir the solution for 1.5 hours at −78° C. After 1.5 hours add above solution to the first refluxing reaction mixture. Again, reflux the reaction mixture for 2 hours more. Evaporate all THF under vacuum and extract the reaction mixture by taking it in ethyl acetate and washing with saturated aqueous sodium chloride. Dry the organic phase over Na2SO4, filter and concentrate under vacuum to give the crude compound. Pass the crude through silica gel (60-120 mesh) column to elute the pure compound. Yield (0.180 g, 33%), 1H NMR (400 MHz, CDCl3) δ 8.863 (s, 1H), 8.663 (d, J=4.8 Hz 1H), 8.621 (d, J=5.6 Hz, 1H), 8.207 (s, 1H), 7.832 (d, J=7.6 Hz, 1H), 7.595 (t, J=5.6 Hz 3H), 7.508 (t, J=7.6 Hz, 1H), 0.286 (s, 9H); MS (ES) m/z 420.17 [M+1]+.

Prepare the following intermediate with procedures similar to those used for 2-chloro-4-[7-(3-trimethylsilanylethynyl-pyridin-4-yl)-benzo[b]-thiophen-2-yl]-pyrimidine.

| Prep | Compound name | MS (ES) [M + 1]+ |
|---|---|---|
| 82 | 2-Chloro-4-[7-(3-trimethylsilanylethynyl-pyridin-4-yl)-benzo[b]thiophen-2-yl]-5-fluoro-pyrimidine | 438 |

Prepare the following intermediates essentially according to the preparation of 1-(2-{4-[7-(5-dimethylaminomethyl-2-fluoro-pyridin-4-yl)-benzo[b]thiophen-2-yl]-5-fluoro-pyrimidin-2-ylamino}-ethyl)-imidazolidin-2-one below using the appropriate starting material.

| Prep | Compound name | Physical Data MS (ES) m/z [M + 1]+ |
|---|---|---|
| 83 | [6-Fluoro-4-(2-{5-methyl-2-[2-(2-oxo-imidazolidin-1-yl)-ethylamino]-pyrimidin-4-yl}-benzo[b]thiophen-7-yl)-pyridin-3-ylmethyl]-methyl-carbamic acid tert-butyl ester | 592 |
| 84 | [6-Fluoro-4-(2-{5-fluoro-2-[2-(2-oxo-imidazolidin-1-yl)-ethylamino]-pyrimidin-4-yl}-benzo[b]thiophen-7-yl)-pyridin-3-ylmethyl]-(3,3,3-trifluoro-propyl)-carbamic acid tert-butyl ester | 678 |
| 85 | (2-Cyano-ethyl)-[6-fluoro-4-(2-{5-fluoro-2-[2-(2-oxo-imidazolidin-1-yl)-ethylamino]-pyrimidin-4-yl}-benzo[b]thiophen-7-yl)-pyridin-3-ylmethyl]-carbamic acid tert-butyl ester | 635 |
| 86 | 1-{2-[4-(7-Bromo-benzo[b]thiophen-2-yl)-5-fluoro-pyrimidin-2-ylamino]-ethyl}-imidazolidin-2-one | 436 |
| 87 | 1-{2-[4-(7-Bromo-benzo[b]thiophen-2-yl)-5-chloro-pyrimidin-2-ylamino]-ethyl}-imidazolidin-2-one | 454 |
| 88 | 1-{2-[4-(7-Bromo-benzo[b]thiophen-2-yl)-5-methyl-pyrimidin-2-ylamino]-ethyl}-imidazolidin-2-one | 434 |
| 89 | 1-{2-[4-(7-Bromo-benzo[b]thiophen-2-yl)-pyrimidin-2-ylamino]-ethyl}-imidazolidin-2-one | 420 |
| 90 | 1-{2-[5-Fluoro-4-(7-{2-fluoro-5-[2-(tetrahydro-pyran-2-yloxy)-ethoxy]-pyridin-4-yl}-benzo[b]thiophen-2-yl)-pyrimidin-2-ylamino]-ethyl}-imidazolidin-2-one | 619 |

Preparation 91

1-(2-[4-[7-(3-Trimethylsilanylethynyl-pyridin-4-yl)-benzo[b]-thiophen-2-yl]-pyrimidin-2-yl-amino)-ethyl imidazolidin-2-one Add 2-chloro-4-[7-(3-trimethylsilanylethynyl-pyridin-4-yl)-benzo[b]-thiophen-2-yl]-pyrimidine (0.180 g, 0.4 mmol) to a sealed tube and add n-butanol (2 mL) to it. Add N-2-amino ethyl imidazolidin-2-one (0.103 g, 0.8 mmol). Seal the tube and heat in an oil bath for 4-5 hours at 120° C. Concentrate the reaction mixture under reduced pressure and purify the crude through column chromatography. Yield (0.1 g, 49%); 1H NMR (400 MHz, DMSO-d6) δ 8.832 (s, 1H), 8.725 (d, J=5.2 Hz, 1H), 8.394 (s, 1H), 8.369 (s, 1H), 8.015 (d, J=8.8 Hz 1H), 7.711 (d, J=5.2 Hz, 1H), 7.552 (m, 2H), 7.356 (s, 1H), 7.272 (d, J=4.8 Hz, 1H), 6.288 (s, 1H), 3.185 (m, 4H), 0.286 (s, 9H); MS (ES) m/z 513 [M+1]+.

Prepare the following intermediate with procedures similar to those used for 1-(2-[4-[7-(3-trimethylsilanylethynyl-pyridin-4-yl)-benzo[b]-thiophen-2-yl]-pyrimidin-2-yl-amino)-ethyl imidazolidin-2-one.

| Prep | Compound name | Physical Data MS (ES) m/z [M + 1]+ |
|---|---|---|
| 92 | 1-(2-[4-[7-(3-Trimethylsilanylethynyl-pyridin-4-yl)-benzo[b]-thiophen-2-yl]-pyrimidin-2-yl-amino)-ethyl imidazolidin-2-one | 531 |

Preparation 93

1-(2-{5-Fluoro-4-[7-(4,4,5,5-tetramethyl-[1,3,2]di-oxaborolan-2-yl)-benzo[b]thiophen-2-yl]-pyrimidin-2-ylamino}-ethyl)-imidazolidin-2-one Combine 7-1-{2-[4-(7-bromo-benzo[b]thiophen-2-yl)-5-fluoro-pyrimidin-2-ylamino]-ethyl}-imidazolidin-2-one (5.5 g, 12.6 mmol), bis(pinacolato)diboron (3.84 g, 15.3 mmol), (1,1'-bis(diphenylphosphino)-ferrocene)dichloropalladium (II) (1.0 g, 1.3 mmol), potassium acetate (2.5 g, 25 mmol) in DMSO (80 mL) in a flask. Bubble nitrogen through the mixture for 10 min. Seal the flask and put it into an oil bath to heat at 85° C. overnight. Dilute the mixture with chloroform/isopropyl alcohol (3/1). Wash the solution with saturated aqueous sodium chloride. Dry it over sodium sulfate. Concentrate the solution in vacuo to a dark residue. Purify the residue by column chromatography (hexane→20% ethyl acetate in hexane→10% methanol in dichloromethane) to afford the product as a brown solid (5 g, 82%). MS (ES) m/z 484 [M+1]$^+$.

Prepare the following compounds with procedures similar to those described for 1-(2-{5-fluoro-4-[7-(4,4,5,5-tetramethyl-[1,3,2]dioxaborolan-2-yl)-benzo[b]thiophen-2-yl]-pyrimidin-2-ylamino}-ethyl)-imidazolidin-2-one.

| Prep | Compound name | Physical Data MS (ES) m/z [M + 1]$^+$ |
|---|---|---|
| 94 | 1-(2-{5-Methyl-4-[7-(4,4,5,5-tetramethyl-[1,3,2]dioxaborolan-2-yl)-benzo[b]thiophen-2-yl]-pyrimidin-2-ylamino}-ethyl)-imidazolidin-2-one | 500 |
| 95 | 1-(2-{5-Chloro-4-[7-(4,4,5,5-tetramethyl-[1,3,2]dioxaborolan-2-yl)-benzo[b]thiophen-2-yl]-pyrimidin-2-ylamino}-ethyl)-imidazolidin-2-one | 480 |
| 96 | 1-(2-{4-[7-(4,4,5,5-Tetramethyl-[1,3,2]dioxaborolan-2-yl)-benzo[b]thiophen-2-yl]-pyrimidin-2-ylamino}-ethyl)-imidazolidin-2-one | 466 |

Preparation 97

1-(2-{4-[7-(5-Azidomethyl-2-fluoro-pyridin-4-yl)-benzo[b]thiophen-2-yl]-5-fluoro-pyrimidin-2-ylamino}-ethyl)-imidazolidin-2-one Combine 5-azidomethyl-2-fluoro-4-iodo-pyridine (70 mg, 0.25 mmol) and 1-(2-{5-fluoro-4-[7-(4,4,5,5-tetramethyl-[1,3,2]dioxaborolan-2-yl)-benzo[b]thiophen-2-yl]-pyrimidin-2-ylamino}-ethyl)-imidazolidin-2-one (100 mg, 0.21 mmol) bis(diphenylphosphino)ferrocene)dichloro palladium (8.5 mg, 0.01 mmol) and NaHCO$_3$ (35 mg, 0.41 mmol) in DMSO (87 mL) and water (3 mL). Purge the mixture through nitrogen for 5 min twice. Heat the mixture at 85° C. for 1 hour in an oil bath. Cool to room temperature. Dilute the reaction mixture with chloroform/isopropyl alcohol 93/1), and wash with water and saturated aqueous sodium chloride. Separate the organic layer from the aqueous layer and dry over sodium sulfate. After filtration, remove the organic solvent to give a crude mixture. Purify the crude by column chromatography (10% methanol in dichloromethane) to afford the title compound (105 mg, 100%). MS (ES) m/z 508 [M+1]$^+$.

Prepare the following intermediates with procedures similar to those described for 1-(2-{4-[7-(5-azidomethyl-2-fluoro-pyridin-4-yl)-benzo[b]thiophen-2-yl]-5-fluoro-pyrimidin-2-ylamino}-ethyl)-imidazolidin-2-one.

| Prep | Compound name | MS (ES) [M + 1]$^+$ | Comments |
|---|---|---|---|
| 98 | 1-[2-(4-{7-[5-(1-Azido-ethyl)-2-fluoro-pyridin-4-yl]-benzo[b]thiophen-2-yl}-5-fluoro-pyrimidin-2-ylamino)-ethyl]-imidazolidin-2-one | 522 | |
| 99 | [4-(2-{5-Fluoro-2-[2-(2-oxo-imidazolidin-1-yl)-ethylamino]-pyrimidin-4-yl}-benzo[b]thiophen-7-yl)-6-fluoro-pyridin-3-ylmethyl]-methyl-carbamic acid tert-butyl ester | 596 | |
| 100 | [4-(2-{5-Chloro-2-[2-(2-oxo-imidazolidin-1-yl)-ethylamino]-pyrimidin-4-yl}-benzo[b]thiophen-7-yl)-6-fluoro-pyridin-3-ylmethyl]-methyl-carbamic acid tert-butyl ester | 613 | NaHCO$_3$ used as base |
| 101 | [6-Fluoro-4-(2-{2-[2-(2-oxo-imidazolidin-1-yl)-ethylamino]-pyrimidin-4-yl}-benzo[b]thiophen-7-yl)-pyridin-3-ylmethyl]-methyl-carbamic acid tert-butyl ester | 578 | NaHCO$_3$ used as base |

Preparation 102

Tert-butyl 1-(6-chloro-4-(2-(5-fluoro-2-(2-(2-oxoimidazolidin-1-yl)ethylamino)pyrimidin-4-yl)benzo[b]thiophen-7-yl)pyridin-3-yl)ethylcarbamate In a microwave vial, combine [1-(6-chloro-4-iodo-pyridin-3-yl)-ethyl]-carbamic acid tert-butyl ester (250 mg, 0.65 mmol) and 1-(2-{5-fluoro-4-[7-(4,4,5,5-tetramethyl-[1,3,2]dioxaborolan-2-yl)-benzo[b]thiophen-2-yl]-pyrimidin-2-ylamino}-ethyl)-imidazolidin-2-one (380 mg, 0.78 mmol), bis(diphenylphosphino)ferrocene)dichloro palladium (53 mg, 0.07 mmol) and NaHCO$_3$ (110 mg, 1.31 mmol) in acetonitrile (7 mL) and water (3 mL). Purge the mixture with nitrogen for 5 min. Heat the mixture at 100° C. for 15 min in a microwave. Remove solvent on a rotovap. Purify by normal phase column chromatography using 0.5% to 5% MeOH in dichloromethane to get off white solid product (220 mg). MS (ES) m/z 612 [M+1]$^+$

Preparation 103

Tert-butyl (6-fluoro-4-(2-(5-fluoro-2-(2-(2-oxo-2,3-dihydro-1H-imidazol-1-yl)ethylamino)pyrimidin-4-yl)benzo[b]thiophen-7-yl)pyridin-3-yl)methyl(methyl)carbamate Combine {4-[2-(2-chloro-5-fluoro-pyrimidin-4-yl)-benzo[b]thiophen-7-yl]-6-fluoro-pyridin-3-ylmethyl}-methyl-carbamic acid tert-butyl ester (0.52 g, 1.04 mmol) and triethylamine (0.87 mL, 6.24 mmol) in n-butanol (10.0 mL). Add 1-(2-amino-ethyl)-1,3-dihydro-imidazol-2-one; compound with trifluoro-acetic acid (0.75 g, 3.12 mmol). Heat the reaction mixture at 120° C. for 54 hours for completion, then cool to room temperature. Remove solvent on a rotovap to obtain the crude product. Purify the crude by column chromatography (0.5% to 6% 2 M NH$_3$ in methanol solution in dichloromethane) to afford the desired product (0.28 g). MS (ES) m/z 594 [M+1]$^+$.

EXAMPLES

Example 1

1-(2-{4-[7-(5-((Dimethylamino)methyl)-2-fluoro-pyridin-4-yl)benzo[b]thiophen-2-yl]-5-fluoropyrimidin-2-ylamino}ethyl)imidazolidin-2-one

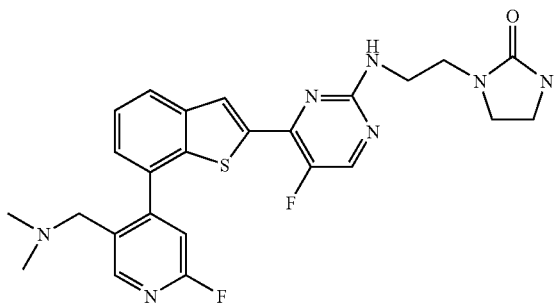

Combine {4-[2-(2-chloro-5-fluoro-pyrimidin-4-yl)-benzo[b]thiophen-7-yl]-6-fluoro-pyridin-3-ylmethyl}-dimethylamine (0.25 g, 0.59 mmol) and triethylamine (0.25 mL, 1.78 mmol) in n-butanol (8.0 mL). Add 1-(2-aminoethyl) imidazolidin-2-one (0.23 g, 1.78 mmol). Heat the reaction mixture at 120° C. overnight (15 hours), then cool to room temperature. Dilute the reaction mixture with ethyl acetate, and wash with water and saturated aqueous sodium chloride. Separate the organic layer from aqueous layer and dry over MgSO$_4$. After filtration, remove the organic solvent to give a crude. Purify the crude by column chromatography (0.5% to 10% 2 N NH$_3$ in methanol solution/dichloromethane) to afford the title compound (0.19 g, 63%). MS (ES) m/z 510 [M+1]$^+$.

Prepare the following compounds essentially according to the preparation of 1-(2-{4-[7-(5-((dimethylamino)methyl)-2-fluoro-pyridin-4-yl)benzo[b]thiophen-2-yl]-5-fluoropyrimidin-2-ylamino}ethyl)imidazolidin-2-one using the appropriate starting material.

| Ex | Compound name | Structure | Physical Data MS (ES) m/z [M + 1]$^+$ |
|---|---|---|---|
| 2 | 1-(2-{4-[7-(2-Fluoro-5-(morpholinomethyl)-pyridin-4-yl)benzo[b]thiophen-2-yl]pyrimidin-2-ylamino}ethyl)imidazolidin-2-one | 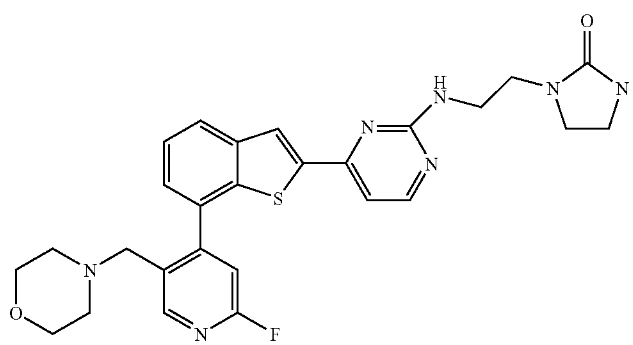 | 534 |
| 3 | 1-(2-{5-Fluoro-4-[7-(2-fluoro-5-(morpholinomethyl)pyridin-4-yl)benzo[b]thiophen-2-yl]-pyrimidin-2-ylamino}ethyl)imidazolidin-2-one | 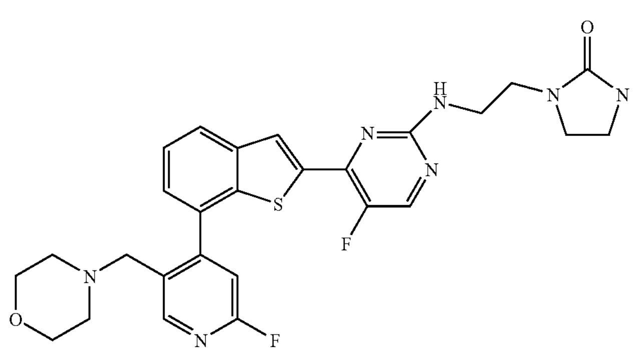 | 552 |

-continued

| Ex | Compound name | Structure | Physical Data MS (ES) m/z [M + 1]⁺ |
|---|---|---|---|
| 4 | 1-(2-{4-[7-(5-((Dimethylamino)methyl)-2-fluoropyridin-4-yl)benzo[b]thiophen-2-yl]pyrimidin-2-ylamino}ethyl)imidazolidin-2-one | 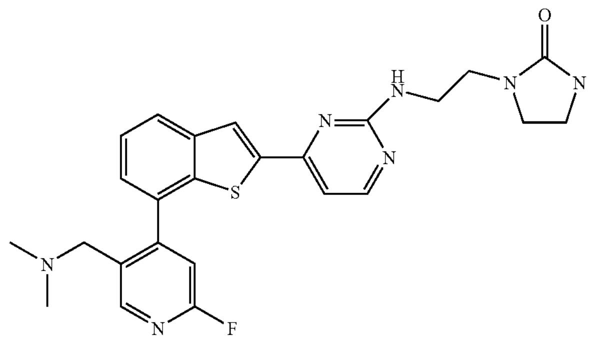 | 492 |
| 5 | 1-(2-{5-Fluoro-4-[7-(3-(morpholinomethyl)-pyridin-4-yl)benzo[b]thiophen-2-yl]pyrimidin-2-ylamino}ethyl)imidazolidin-2-one | 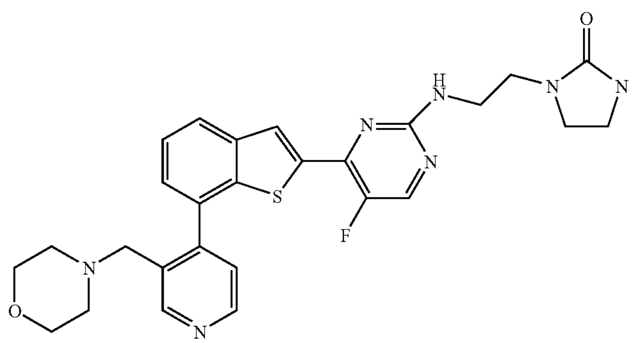 | 534 |
| 6 | 1-(2-{4-[7-(5-(1,3-Dioxolan-2-yl)-2-fluoropyridin-4-yl)benzo[b]thiophen-2-yl]-5-fluoropyrimidin-2-ylamino}ethyl)imidazolidin-2-one | 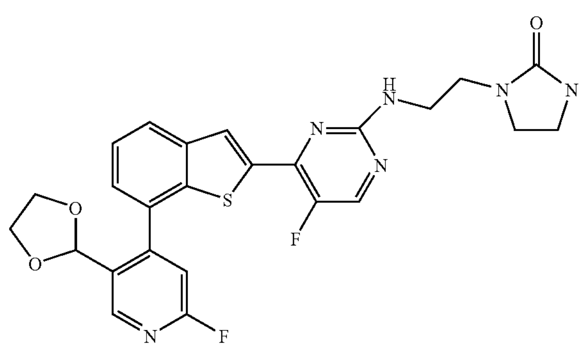 | 525 |
| 7 | 1-(2-{5-Fluoro-4-[7-(2-fluoro-3-((methoxymethoxy)methyl)-pyridin-4-yl)benzo[b]thiophen-2-yl]pyrimidin-2-ylamino}ethyl)imidazolidin-2-one | 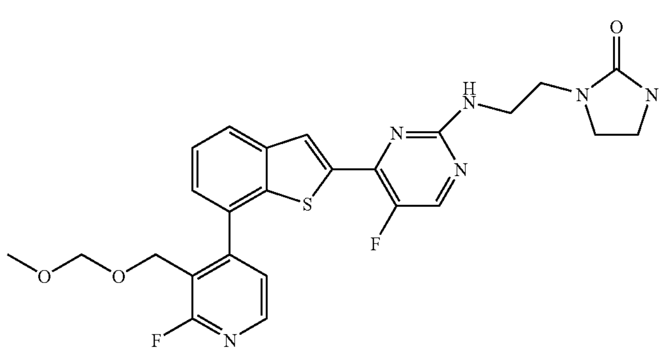 | 527 |

| Ex | Compound name | Structure | Physical Data MS (ES) m/z [M + 1]+ |
|---|---|---|---|
| 8 | 1-(2-{4-[7-(5-Cyclopropyl-2-fluoropyridin-4-yl)benzo[b]thiophen-2-yl]-5-fluoropyrimidin-2-ylamino}ethyl)imidazolidin-2-one | 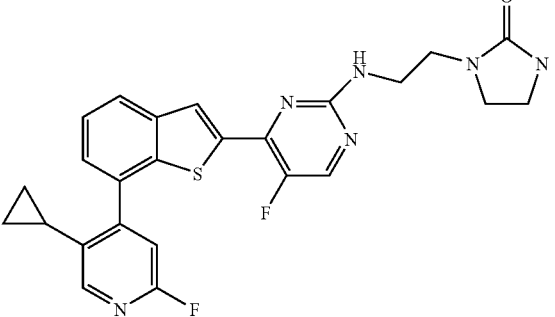 | 493 |

Prepare the following examples with procedures similar to those described for 1-(2-{4-[7-(5-azidomethyl-2-fluoro-pyridin-4-yl)-benzo[b]thiophen-2-yl]-5-fluoro-pyrimidin-2-ylamino}-ethyl)-imidazolidin-2-one.

| Ex | Compound name | Structure | MS (ES) [M + 1]+ |
|---|---|---|---|
| 9 | 1-(2-{5-Fluoro-4-[7-(2-fluoro-5-(pyrrolidin-1-ylmethyl)pyridin-4-yl)benzo[b]thiophen-2-yl]pyrimidin-2-ylamino}ethyl)imidazolidin-2-one | 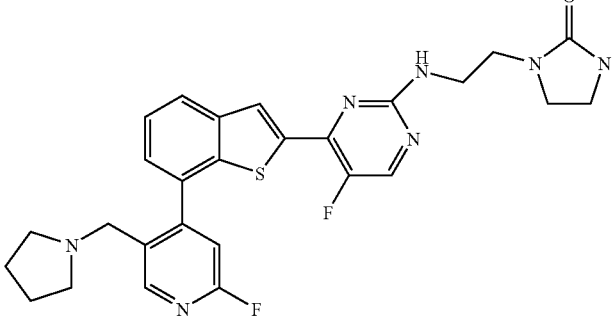 | 536 |
| 10 | 1-(2-{4-[7-(5-(Azetidin-1-ylmethyl)-2-fluoropyridin-4-yl)benzo[b]thiophen-2-yl]-5-fluoropyrimidin-2-ylamino}ethyl)imidazolidin-2-one | 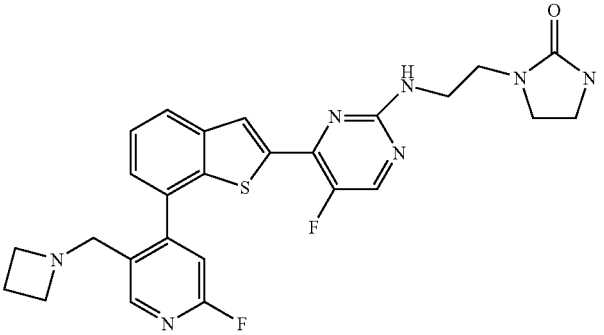 | 522 |

| Ex | Compound name | Structure | MS (ES) [M + 1]+ |
|---|---|---|---|
| 11 | 1-(2-{5-Chloro-4-[7-(5-((dimethylamino)methyl)-2-fluoropyridin-4-yl)benzo[b]thiophen-2-yl]pyrimidin-2-ylamino}ethyl)imidazolidin-2-one | 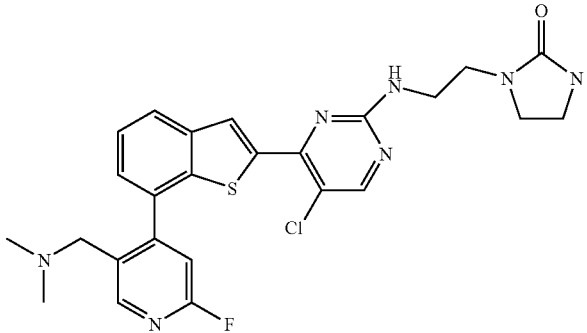 | 527 |
| 12 | 1-{2-[5-Fluoro-4-(7-{2-fluoro-5-[(2-hydroxy-ethylamino)-methyl]pyridin-4-yl}benzo[b]thiophen-2-yl)pyrimidin-2-ylamino]-ethyl}imidazolidin-2-one | 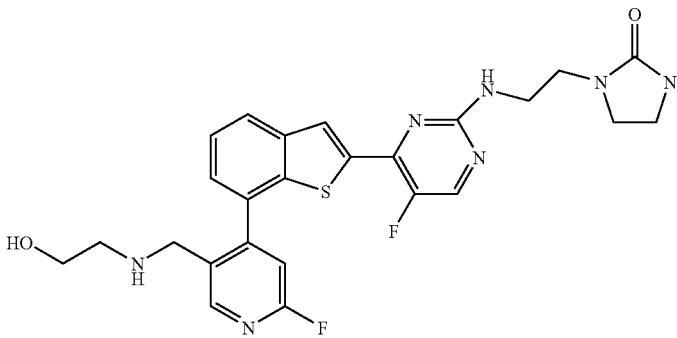 | 526 |
| 13 | 1-(2-{5-Fluoro-4-[7-(2-fluoro-5-((propylamino)methyl)pyridin-4-yl)benzo[b]thiophen-2-yl]pyrimidin-2-ylamino}ethyl)imidazolidin-2-one | 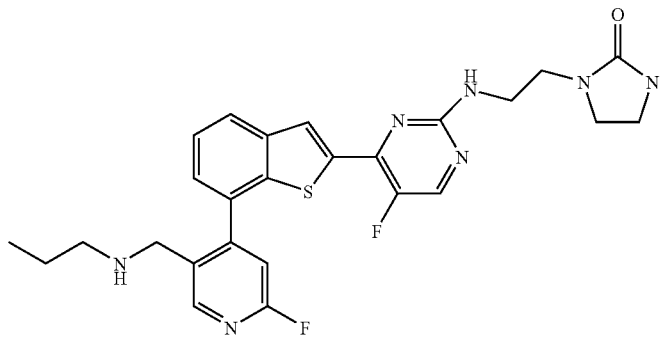 | 524 |

-continued

| Ex | Compound name | Structure | MS (ES) [M + 1]+ |
|---|---|---|---|
| 14 | 1-(2-(4-(7-(5-((Ethylamino)methyl)-2-fluoropyridin-4-yl)benzo[b]thiophen-2-yl)-5-fluoropyrimidin-2-ylamino)ethyl)imidazolidin-2-one | 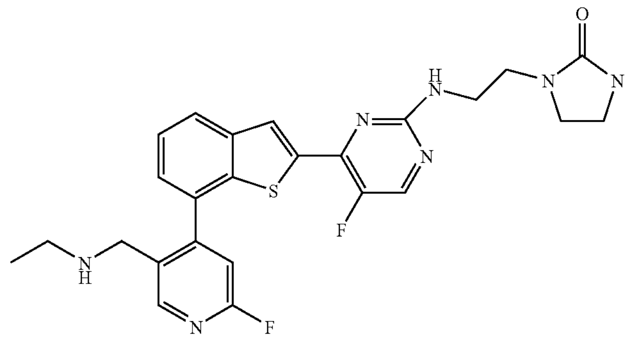 | 510 |
| 15 | 1-{2-[4-(7-{5-[(Ethyl(methyl)amino)-methyl]-2-fluoropyridin-4-yl}benzo[b]thiophen-2-yl)-5-fluoropyrimidin-2-ylamino]ethyl}imidazolidin-2-one | 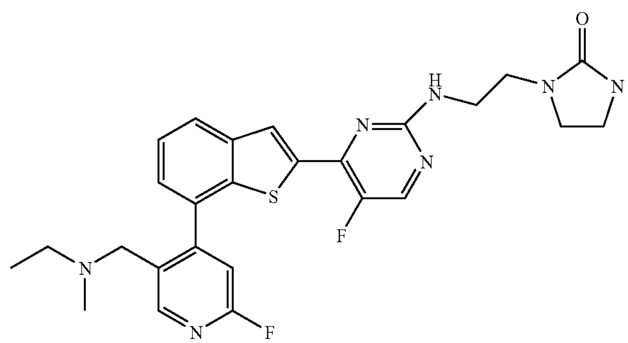 | 524 |
| 16 | 1-(2-{4-[7-(5-((Diethylamino)methyl)-2-fluoropyridin-4-yl)benzo[b]thiophen-2-yl]-5-fluoropyrimidin-2-ylamino}ethyl)imidazolidin-2-one | 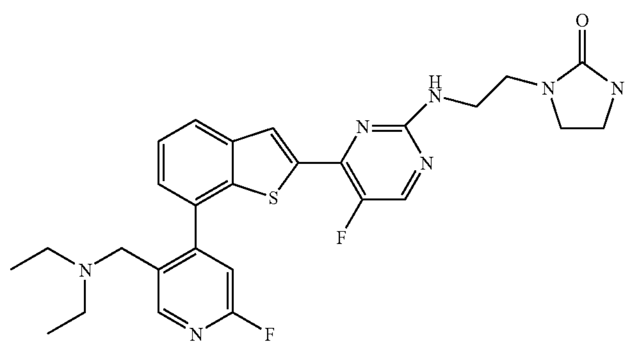 | 538 |
| 17 | 1-(2-{4-[7-(5-((Dimethylamino)methyl)-2-fluoropyridin-4-yl)-benzo[b]thiophen-2-yl]-5-methylpyrimidin-2-ylamino}ethyl)imidazolidin-2-one | 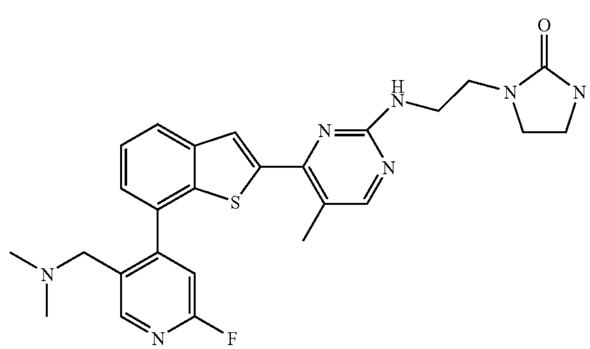 | 506 |

Example 18

1-(2-{5-Fluoro-4-[7-(2-fluoro-5-((methylamino)methyl)pyridin-4-yl)benzo[b]thiophen-2-yl]-pyrimidin-2-ylamino}ethyl)imidazolidin-2-one

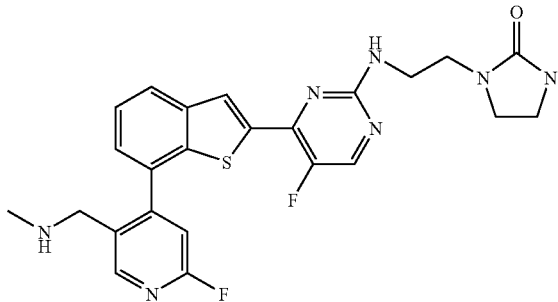

Dissolve [4-(2-{5-fluoro-2-[2-(2-oxo-imidazolidin-1-yl)-ethylamino]-pyrimidin-4-yl}-benzo[b]thiophen-7-yl)-6-fluoro-pyridin-3-ylmethyl]-methyl-carbamic acid tert-butyl ester (0.19 g, 0.32 mmol) in dry $CH_2Cl_2$ (1.4 mL) and $CF_3COOH$ (1.4 mL). Stir at room temperature for 1 hour. Remove solvent completely. Dilute the trifluoro-acetic acid salt with $CH_2Cl_2$. Wash with saturated $NaHCO_3$ solution, water and saturated aqueous sodium chloride. Dry with $MgSO_4$. After filtration, remove solvent. Dry in vacuo overnight to afford the title compound (0.12 g, 78%). MS (ES) m/z 495 [M+1]+.

Prepare the following examples with procedures similar to those described for 1-(2-{5-fluoro-4-[7-(2-fluoro-5-methylaminomethyl-pyridin-4-yl)-benzo[b]thiophen-2-yl]-pyrimidin-2-ylamino}-ethyl)-imidazolidin-2-one.

| Ex | Compound name | Structure | MS (ES) [M + 1]+ |
|---|---|---|---|
| 19 | 1-(2-{4-[7-(2-Fluoro-5-((methylamino)methyl)pyridin-4-yl)benzo[b]thiophen-2-yl]-5-methylpyrimidin-2-ylamino}ethyl)imidazolidin-2-one | 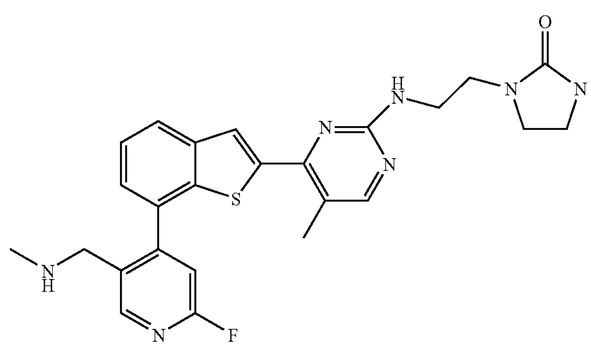 | 492 |
| 20 | 1-(2-{5-Chloro-4-[7-(2-fluoro-5-((methylamino)methyl)pyridin-4-yl)benzo[b]thiophen-2-yl]pyrimidin-2-ylamino}ethyl)imidazolidin-2-one | 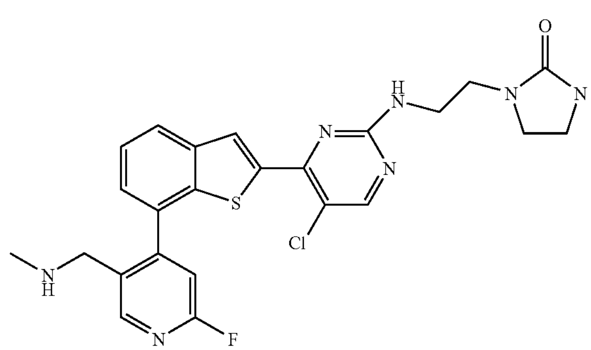 | 512 |
| 21 | 1-(2-{4-[7-(2-Fluoro-5-((methylamino)methyl)pyridin-4-yl)benzo[b]thiophen-2-yl]pyrimidin-2-ylamino}ethyl)imidazolidin-2-one | 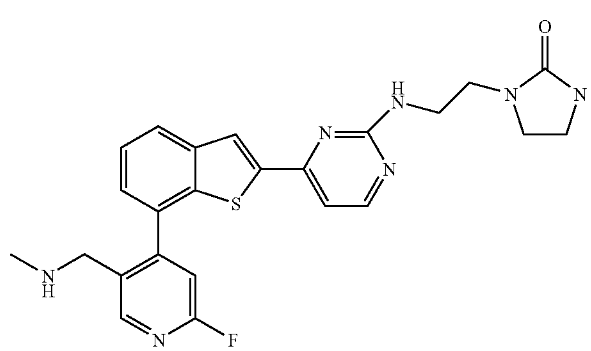 | 478 |

| Ex | Compound name | Structure | MS (ES) [M + 1]+ |
|---|---|---|---|
| 22 | 1-[2-(4-{7-[5-(1-Aminoethyl)-2-fluoropyridin-4-yl]benzo[b]thiophen-2-ylamino)ethyl]imidazolidin-2-one | 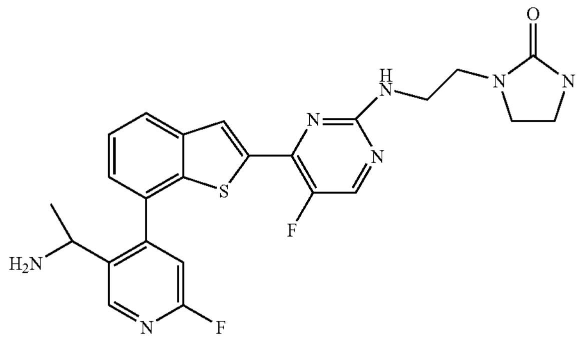 | 494 |

Example 23

1-(2-{5-Fluoro-4-[7-(2-fluoro-5-((methylamino)methyl)pyridin-4-yl)benzo[b]thiophen-2-yl]pyrimidin-2-ylamino}ethyl)-1H-imidazol-2(3H)-one

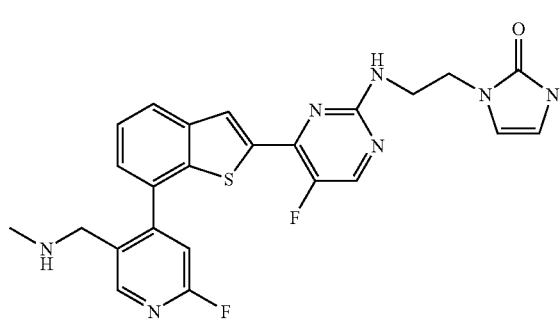

Add trifluoro-acetic acid (1 mL) to a solution of [6-fluoro-4-(2-{5-fluoro-2-[2-(2-oxo-2,3-dihydro-imidazol-1-yl)-ethylamino]-pyrimidin-4-yl}-benzo[b]thiophen-7-yl)-pyridin-3-ylmethyl]-methyl-carbamic acid tert-butyl ester (280 mg, 0.47 mmol) in dichloromethane (1 mL). Stir for 1 hour and remove solvent on a rotovap. Wash with saturated NaHCO₃ and extract in dichloromethane, wash with saturated aqueous sodium chloride, dry over Na₂SO₄, and filter. Remove solvent on a rotovap to obtain the solid and dry under vacuum to afford the product (196 mg). MS (ES) m/z 494 [M+1]+.

Example 24

1-{2-[5-Fluoro-4-(7-{2-fluoro-5-[(3,3,3-trifluoro-propylamino)-methyl]-pyridin-4-yl}benzo[b]thiophen-2-yl)pyrimidin-2-ylamino]ethyl}imidazolidin-2-one

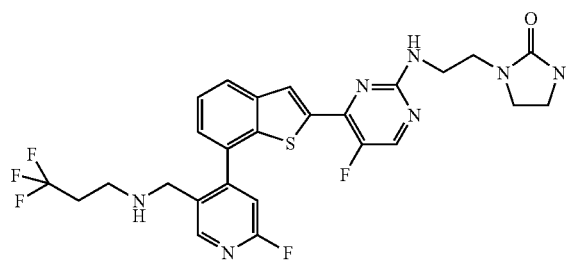

Add hydrogen chloride (2 mL, 1 M in diethyl ether) to a solution of [6-fluoro-4-(2-{5-fluoro-2-[2-(2-oxo-imidazolidin-1-yl)-ethylamino]-pyrimidin-4-yl}-benzo[b]thiophen-7-yl)-pyridin-3-ylmethyl]-(3,3,3-trifluoro-propyl) carbamic acid tert-butyl ester (0.136 g, 200.68 μmol) in dichloromethane (3 mL). Stir the mixture overnight at room temperature. Evaporate the solvent and suspend the resulting solid in dichloromethane and treat with 30% aqueous potassium carbonate. Wash the organic phase with saturated aqueous sodium chloride and load the organic solution onto a 25 g silica gel loading column with dichloromethane and elute onto a 40 g silica gel column with a gradient from dichloromethane to ethyl acetate and then from ethyl acetate to 10% methanol in ethyl acetate to give the title compound. Purify the material further by HPLC (HPLC Conditions: 38-42% CH₃CN/10 mM NH₄HCO₃, pH 10 at 20 mL/min on XBride® MS C₁₈ 19×100 mm) Collect the appropriate fractions and concentrate it. Co-evaporate the residue with two portions absolute ethanol, one portion toluene, and transfer to a 10 mL round bottom with dichloromethane. Convert the material to a solid using dichloromethane hexane co-evaporation to give the title compound 45 mg (39%) as a yellow solid. MS (ES) m/z 578 [M+1]+.

Prepare the following example with procedures similar to those described for 1-{2-[5-fluoro-4-(7-{2-fluoro-5-[(3,3,3-trifluoro-propylamino)-methyl]-pyridin-4-yl}benzo[b]thiophen-2-yl)pyrimidin-2-ylamino]ethyl}imidazolidin-2-one.

| Ex | Compound Name | Structure | MS (ES) [M + 1]+ |
|---|---|---|---|
| 25 | 3-{[6-Fluoro-4-(2-{5-fluoro-2-[2-(2-oxoimidazolidin-1-yl)ethylamino]pyrimidin-4-yl}benzo[b]thiophen-7-yl)pyridin-3-yl]methylamino}-propanenitrile | 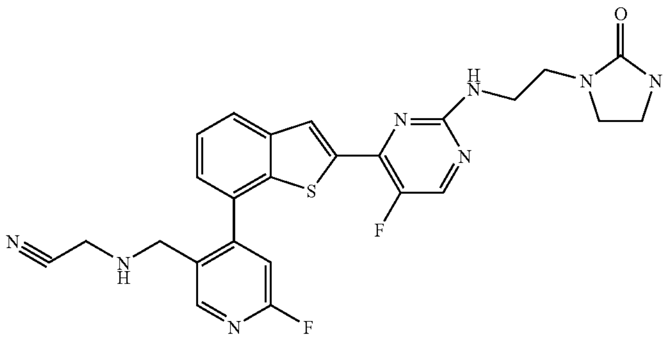 | 535 |

Example 26

1-(2-{4-[7-(5-(Aminomethyl)-2-fluoropyridin-4-yl)benzo[b]thiophen-2-yl]-5-fluoropyrimidin-2-ylamino}ethyl)imidazolidin-2-one

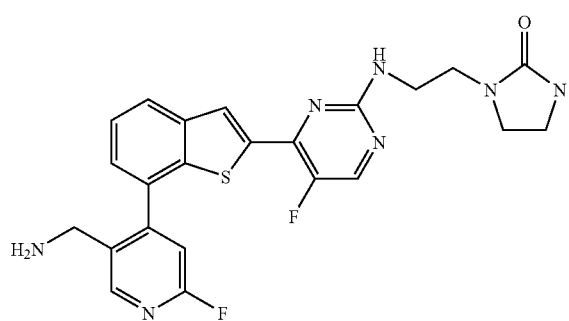

To a solution of 1-(2-{4-[7-(5-azidomethyl-2-fluoro-pyridin-4-yl)-benzo[b]thiophen-2-yl]-5-fluoro-pyrimidin-2-ylamino}-ethyl)-imidazolidin-2-one (105 mg, 0.3 mmol) in ethanol (10 mL) in a round bottom flask add 2 g hydrazine formic acid salt (1:1) and 0.5 g of Raney Nickel. Stir the mixture for 3 hours at room temperature. Pour the reaction mixture diluted sodium carbonate solution. Abstract the product into chloroform, and wash with water and saturated aqueous sodium chloride. Separate organic layer from aqueous layer and dry over Na$_2$SO$_4$. After filtration, evaporate the organic solvent in vacuo to give a crude product. Purify the crude with flash column chromatography (chloroform/methanol/ammonium hydroxide, 7/3/0.05) to give the title compound as a yellow solid (0.50 mg, 53%). MS (ES) m/z 482 [M+1]+.

Examples 27 and 28

R-1-[2-(4-{7-[5-(1-Aminoethyl)-2-fluoropyridin-4-yl]benzo[b]thiophen-2-yl}-5-fluoropyrimidin-2-ylamino)ethyl]imidazolidin-2-one and S-1-[2-(4-{7-[5-(1-Aminoethyl)-2-fluoropyridin-4-yl]benzo[b]thiophen-2-yl}-5-fluoropyrimidin-2-ylamino)ethyl]imidazolidin-2-one Separate 1-[2-(4-{7-[5-(1-aminoethyl)-2-fluoropyridin-4-yl]benzo[b]thiophen-2-yl}-5-fluoropyrimidin-2-ylamino)ethyl]imidazolidin-2-one (180 mg, 0.36 mmol) by chiral HPLC (Chiralpak® AD-H, 9/1 EtOH/acetonitrile, 0.2% N,N-dimethylethanolamine, 1 mL/min, 225 nm) to give the first fraction as the S-enantiomer (50 mg, 28%) and the second fraction as the R-enantiomer (51 mg, 28%). MS (ES) m/z 496 [M+1]+.

Example 29

1-[2-(5-Fluoro-4-{7-[2-fluoro-5-(2-hydroxyethoxy) pyridin-4-yl]benzo[b]thiophen-2-yl}pyrimidin-2-ylamino)ethyl]imidazolidin-2-one

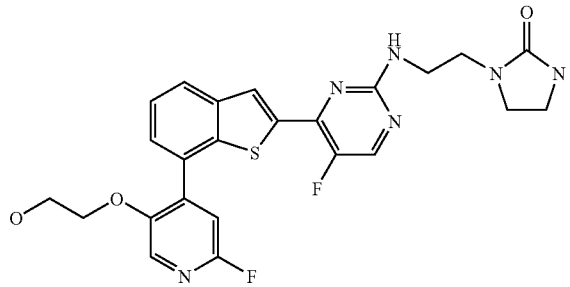

Add pyridinium p-toluenesulfonate (4.3 mg, 0.02 mmol) to a solution of 1-{2-[5-fluoro-4-(7-{2-fluoro-5-[2-(tetrahydro-pyran-2-yloxy)-ethoxy]-pyridin-4-yl}-benzo[b]thiophen-2-yl)-pyrimidin-2-ylamino]-ethyl}-imidazolidin-2-one (100 mg, 0.17 mmol) in ethanol (4 mL). Stir the mixture at 55° C. overnight. Cool the solution. Concentrate the solution in vacuo to yellow oil. Purify the oil by column chromatography (methylene chloride to 10% methanol in methylene chloride) to afford the title compound (75 mg, 87%) as a light yellow solid. MS (ES) m/z 513 [M+1]+.

Example 30

1-(2-(4-(7-(3-Ethynylpyridin-4-yl)benzo[b]thiophen-2-yl)pyrimidin-2-ylamino)ethyl)imidazolidin-2-one

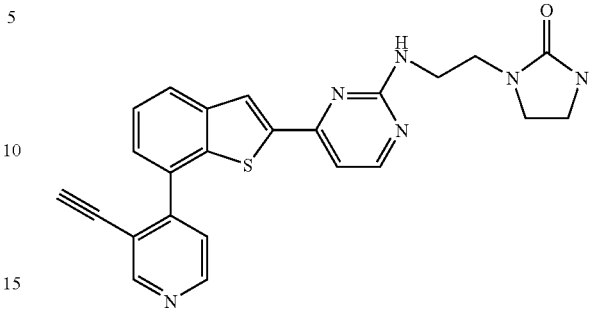

Add 1-(2-[4-[7-(3-trimethylsilanylethynyl-pyridin-4-yl)-benzo[b]-thiophen-2-yl]-pyrimidin-2-yl-amino)-ethyl imidazolidin-2-one (0.1 g, 0.19 mmol) in methanol in a round bottom flask. Add potassium carbonate (0.053 g, 0.38 mmol). Stir the reaction mixture at room temperature for 20 min. Evaporate all the solvent under vacuum. Extract the compound by diluting with dichloromethane and washing with water. Dry the compound under vacuum (0.083 g, 40%). MS (ES) m/z 441.26 [M+1]+.

Prepare the following example with procedures similar to those used for 1-(2-(4-(7-(3-ethynylpyridin-4-yl)benzo[b]thiophen-2-yl)pyrimidin-2-ylamino)ethyl)imidazolidin-2-one.

| Ex | Compound Name | Structure | MS (ES) [M + 1]+ |
|---|---|---|---|
| 31 | 1-(2-(4-(7-(3-Ethynylpyridin-4-yl)benzo[b]thiophen-2-yl)-5-fluoropyrimidin-2-ylamino)ethyl)imidazolidin-2-one | 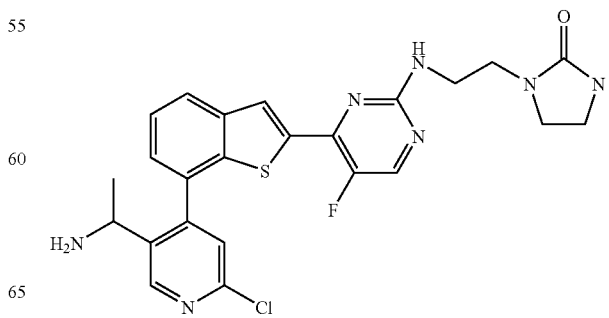 | 459 |

Example 32

1-(2-(4-(7-(5-(1-Aminoethyl)-2-chloropyridin-4-yl) benzo[b]thiophen-2-yl)-5-fluoropyrimidin-2-ylamino)ethyl)imidazolidin-2-one Add trifluoro-acetic acid (1 mL) to a solution of tert-butyl 1-(6-chloro-4-(2-(5-fluoro-2-(2-(2-oxoimidazolidin-1-yl)ethylamino)pyrimidin-4-yl)benzo[b]thiophen-7-yl)pyridin-3-yl)ethylcarbamate (220 mg, 0.36 mmol) in dichloromethane (1 mL). Stir for 1 hour and remove solvent on a rotovap. Wash with saturated NaHCO$_3$ and extract in dichloromethane, wash with saturated aqueous sodium chloride, dry over Na$_2$SO$_4$, and filter. Remove solvent on a rotovap to obtain the solid and dry under vacuum to afford the product (158 mg). MS (ES) m/z 512 [M+1]$^+$.

Separate the product (90 mg, 0.18 mmol) by chiral HPLC (Chiralpak® AS-H, 100% MeOH/0.02% dimethylethanolamine \CO$_2$, 5 mL/min, 225 nm) to obtain the first eluted isomer (39 mg). MS (ES) m/z 512 [M+1]$^+$.

Example 33 and 34

S-1-(2-(4-(7-(5-(1-(Ethylamino)ethyl)-2-fluoropyridin-4-yl)benzo[b]thiophen-2-yl)-5-fluoropyrimidin-2-ylamino)ethyl)imidazolidin-2-one and R-1-(2-(4-(7-(5-(1-(Ethylamino)ethyl)-2-fluoropyridin-4-yl)benzo[b]thiophen-2-yl)-5-fluoropyrimidin-2-ylamino)ethyl)imidazolidin-2-one

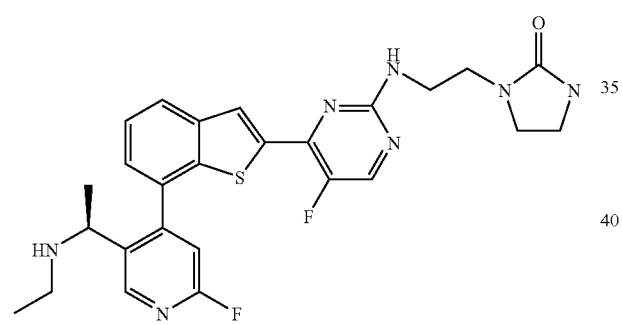

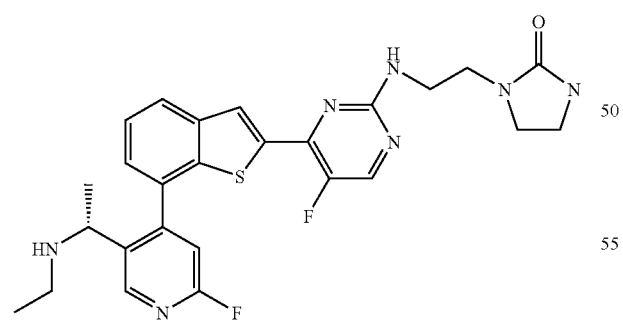

Separate 1-(2-(4-(7-(5-(1-(ethylamino)ethyl)-2-fluoropyridin-4-yl)benzo[b]thiophen-2-yl)-5-fluoropyrimidin-2-ylamino)ethyl)imidazolidin-2-one (150 mg, 0.29 mmol) by chiral HPLC (Chiralpak® AD-H 30% MeOH/0.2% isopropylamine/CO$_2$ 5 mL/min 225 nm) to give the first fraction as the S-enantiomer (58.4 mg, 38%) and the second fraction as R-enantiomer (58.4 mg, 38%). MS (ES) m/z 524 [M+1]$^+$.

Example 35 and 36

S-1-(2-(5-Fluoro-4-(7-(2-fluoro-5-(1-(methylamino)ethyl)pyridin-4-yl)benzo[b]thiophen-2-yl)pyrimidin-2-ylamino)ethyl)imidazolidin-2-one and R-1-(2-(5-Fluoro-4-(7-(2-fluoro-5-(1-(methylamino)ethyl)pyridin-4-yl)benzo[b]thiophen-2-yl)pyrimidin-2-ylamino)ethyl)imidazolidin-2-one

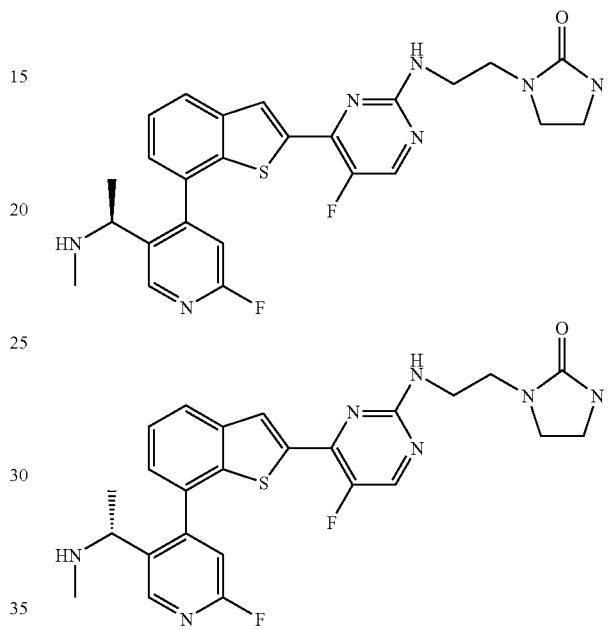

Prepare 1-(2-(5-fluoro-4-(7-(2-fluoro-5-(1-(methylamino)ethyl)pyridin-4-yl)benzo[b]thiophen-2-yl)pyrimidin-2-ylamino)ethyl)imidazolidin-2-one with procedures similar to those described for 1-(2-{5-fluoro-4-[7-(2-fluoro-5-methylaminomethyl-pyridin-4-yl)-benzo[b]thiophen-2-yl]-pyrimidin-2-ylamino}-ethyl)-imidazolidin-2-one. Separate 1-(2-(5-fluoro-4-(7-(2-fluoro-5-(1-(methylamino)ethyl)pyridin-4-yl)benzo[b]thiophen-2-yl)pyrimidin-2-ylamino)ethyl)imidazolidin-2-one (196 mg, 0.38 mmol) by chiral HPLC (Chiralpak® AD-H, 40% EtOH (0.2% isopropylamine)/CO$_2$ 5 mL/min 225 nm) to give the first fraction as the S-enantiomer (60.2 mg, 31%) and the second fraction as the R-enantiomer (58.9 mg, 30%). MS (ES) m/z 510 [M+1]$^+$.

Assays

Plk1 has been shown to be over expressed in many human tumors, such as non-small cell lung, oropharyngeal, oesophageal, gastric, melanoma, breast, ovarian, endometrial, colorectal, glioblastoma, papillary, pancreatic, prostate, hepatoblastoma and non-Hodgkin lymphoma cancers. Furthermore, Plk1 expression has prognostic significance in non-small cell lung, oropharyngeal, oesophageal, melanoma, colorectal, hepatoblastoma and non-Hodgkin lymphoma cancers (Strebhardt, K. and A. Ullrich. *Nature Reviews Cancer* 6(4): 321-30 (2006)). Plk1 phosphorylated substrates regulate progression of mitosis by coordinating centrosome maturation, entry into mitosis, sister chromatid separation and cytokinesis (Eckerdt and Strebhardt 2006; Strebhardt and Ullrich 2006; van de Weerdt, B. C. and R. H. Medema. *Cell Cycle* 5(8): 853-64 (2006)). Inhibiting Plk1 function using antibody injection, expression of a dominant negative Plk1, and antisense mRNA reduction produces monopole spindles and anaphase arrest leading to mitotic cell death in tumor cell lines but reversible G2 arrest in normal non-transformed primary cell lines.

Additionally, it has been reported that Plk may be useful in the treatment of rhabdoid tumors, (Morozov A., et al., Clinical Cancer Research. 13(16):4721-30, (Aug. 15, 2007).

BI-2536 has demonstrated activity in preclinical models using HCT116, A549 and NCIH460 murine xenografts (Baum, A., P. Garin-Chesa, et al. (2006). #C191 *In vivo activity of BI 2536, a potent and selective inhibitor of the mitotic kinase PLK1, in a range of cancer xenografts*. AACR-NCI-EORTC International Conference on "Molecular Targets and Cancer Therapeutics", Philadelphia, Pa.).

The results of the following assays demonstrate evidence that the compounds of the present invention are useful as anticancer agents.

Expression and Purification of Plk1

Human Plk1 cDNA, which may be obtained from a number of sources, such as Incyte (accession number: NM_005030), may be directly linked at one of its termini with a polynucleotide sequence expressing a $His_6$ tag, such as the C-terminal FLAG-$His_6$ tag, and inserted into an appropriate expression vector, such as a pFastBac™ vector (Invitrogen) and transfected into an appropriate system, such as baculovirus similar to what has been reported by Yue-Wei Qian, et al., Science, 282, 1701 (1998) for xPlkk1. If a viral expression system is used, then the virus (e.g., baculovirus bearing a Plk1-Flag-$His_6$ tag polynucleotide construct) is infected into a culture of a suitable host cell, such as Sf9 cells. When sufficient amounts of the Plk1-Flag-$His_6$ tag fusion protein have been expressed, for example, at about 46 hours after infection, the culture should be treated with okadaic acid (0.1 μM) for a sufficient period of time (e.g., 3 hours). The Plk1-Flag-$His_6$ tag fusion is purified from cell pellets using a metal affinity resin, such as TALON™ (Clontech, Catalog# 635503) using methods well known in the art. Purified Plk1-Flag-$His_6$ tag fusion is stored in a suitable medium, such as 10 mM HEPES, 150 mM NaCl, 0.01% TRITON® X-100, 1 mM dithiothreitol (DTT), 10% glycerol, pH 7.5, at −80° C. in small aliquots until use. The identity of the purified Plk1-Flag-$His_6$ tag fusion protein is confirmed by MALDI (Matrix-Assisted Laser Desorption/Ionization).

Expression and Purification of GST-Cdc25C(1-206)

Human Cdc25C cDNA, which may be obtained from any appropriate source, such as Incyte (accession number: AY497474), may be expressed in any convenient expression system, after which purification is effected by well known methods similar to that described by Bin Ouyang et al, Oncogene, 18, 6029-6036 (1999). One convenient system involves overnight growth at 18° C. of *E. coli* BL21 transformed with the pGEX-2T vector (Amersham) into which the cDNA for human Cds25C has been engineered for induced expression using 1 mM isopropyl-beta-D-thiogalactopyranoside. The expressed GST-Cdc25C(1-206), the substrate for Plk1, may be purified by GLUTATHIONE SEPHAROSE® 4B and stored in an appropriate solution, such as 10 mM HEPES, 100 mM NaCl, pH 7.5 in small aliquots at −80° C.

Plk1 Inhibition Assay

Plk1 kinase reactions contain Plk1-Flag-$His_6$ tag fusion enzyme (0.2 ng/μL) in a buffer containing 50 mM HEPES, pH 7.3, 1.0 mM dithiothreitol, 5.0 μM ATP, 10 mM $MgCl_2$, 0.01% TRITON® X-100, 0.4 μCi $^{33}$P-ATP, and 0.06 μg/μL GST-Cdc25c (1-206) peptide. Compounds are provided as 10 mM stocks in DMSO. Compounds are serially diluted 1:3 in 20% DMSO to create a 10-point concentration-response curve and subsequently are diluted 1:5 (20 μM to 0.001 μM final in 4% final DMSO concentration) in the reaction mixture to determine compound activity. The reaction is carried out at room temperature for 60 min and then quenched by adding 60 μL of 10.0% $H_3PO_4$. The reaction mixture (85 μL) is transferred to a 96 well phosphocellulose filter plate pre-wetted with 30 μL of 10.0% $H_3PO_4$, incubated at room temperature for 20-30 min and then washed 3× with 0.5% $H_3PO_4$. Wells are dried before addition of 40 μL of MicroScint™ 20 (Packard) and then counted on a Wallac MICROBETA® Jet. The percentage inhibition values from the 10-point concentration response data are subsequently analyzed, for example, using ACTIVITY BASE™ software (IDBS), using a 4-parameter logistic equation. Absolute $IC_{50}$ values are calculated from the resulting curve fit. All exemplified compounds have an $IC_{50}$ less than 100 nM with a Minimum Significant Ratio (MSR) of 3.6. For example, Example 4 has an $IC_{50}$ of about 25 nM.

pHH3(S10), Mitotic Cells, and DNA Content Assays

HeLa Cells from the American Type Culture Collection (ATCC) are plated at 200 cells/well in 96 well Beckman Dickinson BIOCOAT™ plates, and are incubated in MEM (Minimum Essential Medium, e.g., GIBCO, catalog #11095) with 10% FBS (Fetal Bovine Serum) in 37° C., 5% $CO_2$ for 24 hours. Cells are treated by adding compound (in 0.25% DMSO) to the medium, dosing at 10 points across the range 0.5 μM to 0.0098 μM. After 23 hours exposure to the compounds, cells are fixed, for example with the PREFER™ fixative [Anatech LTD., Catalog #414] for 30 min then are permeablized with 0.1% TRITON® X100 in phosphate buffered saline (PBS) solution for 15 min. Cells are washed 3 times with PBS then digested with 50 μg/mL RNAse. Primary antibody, phosphohistone H3 (Upstate Cat#06-570), is added at 1:500 in PBS with 1% bovine serum albumin (BSA) to the cells over night at 4° C. After 3 PBS washes, cells are incubated with Alexa488 labeled secondary antibody (Invitrogen cat #A11008) for 1 hour at room temperature. Again they are washed 3 times with PBS, and then 15 μM propidium iodide (Molecular Probes cat #P3566) is added for 30 min to stain nuclei. Fluorescence Plates are scanned with ACUMEN EXPLORER™ [Laser-scanning fluorescence microplate cytometer (comprising of 488 nm argon ion laser excitation and multiple photomultiplier tube detection), manufactured by TTP LABTECH LTD] to measure phosphohistone H3, DNA content and mitotic cells as measured by DNA condensation. Image analysis are based on cellular fluorescent signals for identifying cells in different subpopulations. pHH3 (S10) positive cells are identified by mean intensity at 500-530 nm above the threshold. Total intensity at 655-705 nm from propidium iodide/DNA is used to identify individual cells (cells with DNA content from 2N to 4N) and subpopulations in cell cycle (2N cells, 4N cells). Peak intensity at 575-640 nm is used to identify DNA condensation that is used as the marker to identify mitotic cells among 4N cells. Assay outputs are percentage of each identified subpopulations, % pHH3, % 2N, %4N, % mitotic and total cell number. The $EC_{50}$ is determined by curve fitting to a four parameter logistic for each output using ACTIVITY BASE™. The resulting $EC_{50s}$ for pHH3(s10), DNA content, and mitotic have an MSR of 2.6, 2.4 and 2.5, respectively. For example, Example 4 has a pHH3(s10) $EC_{50}$=24 nM (n=1), DNA content $EC_{50}$=35 nM (n=2) and mitotic $EC_{50}$=22 nM (n=1).

Antiproliferative Assay

The effects of compounds on cell proliferation can be determined using cells and cell proliferation methods well-known in the art (Robert C. Squatrito et al., Gynecological Oncology, 58, 101-105, (1995)). For example, HCT116 cells, which may be obtained from the American Type Culture Collection, may be seeded at ~2000 cells/well in 96-well plates and allowed to attach overnight in a humidified $CO_2$ incubator at 37° C. Following the 20-24 hour incubation, half-log serially diluted compounds are added and the plates are returned to the incubator. After an appropriate length of exposure (e.g., 72 hours), cell proliferation is estimated using well-known methods. In one method, 10 μL of a tetrazolium salt, such as Alamar Blue™ is added to the cell plates. After an appropriate exposure to the dye, fluorescence (530 nm excitation, 580 nm emission) is determined. The resulting $IC_{50}$ has an MSR of 3.1. For example, Example 4 has an $IC_{50}$ of 44 nM (n=3).

The compounds of the present invention are preferably formulated as pharmaceutical compositions administered by a variety of routes. Most preferably, such compositions are for oral administration. Such pharmaceutical compositions and processes for preparing same are well known in the art. See, e.g., REMINGTON: THE SCIENCE AND PRACTICE OF PHARMACY (A. Gennaro, et al., eds., 19$^{th}$ ed., Mack Publishing Co., 1995).

The compounds of Formula I are generally effective over a wide dosage range. For example, dosages per day normally fall within the range of about 0.01 to about 20 mg/kg of body weight, preferably 0.1 to 20 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:
1. A compound of the formula:

[Chemical structure]

wherein:
$R^1$ is aminomethyl, ($C_1$-$C_3$ alkyl)aminomethyl, di($C_1$-$C_2$ alkyl)aminomethyl, N-ethyl-N-methyl-aminomethyl, 1-aminoethyl, 1-(($C_1$-$C_2$ alkyl)amino)-ethyl, 3,3,3-trifluoropropylaminomethyl, ethynyl, 2-hydroxy-ethoxy, 2-hydroxyethylaminomethyl, 2-cyanoethylaminomethyl, morpholin-4-ylmethyl, methoxymethoxymethyl, cyclopropyl, 1-azetidinylmethyl, 1-pyrrolidinylmethyl, or 1,3-dioxolan-2-yl;

$R^2$ is hydrogen or halo;
$R^3$ is hydrogen or halo; provided that at least one of $R^2$ and $R^3$ is hydrogen; $R^4$ is hydrogen, methyl, or halo; and
— is a single bond that is either present or absent; or a pharmaceutically acceptable salt thereof.

2. The compound of claim 1 wherein: $R^1$ is aminomethyl, ($C_1$-$C_3$ alkyl)aminomethyl, di($C_1$-$C_2$ alkyl)aminomethyl, N-ethyl-N-methyl-aminomethyl, 1-aminoethyl, 1-(($C_1$-$C_2$ alkyl)amino)-ethyl, 3,3,3-trifluoropropylaminomethyl, ethynyl, 2-hydroxy-ethoxy, 2-hydroxyethylaminomethyl, 2-cyanoethylaminomethyl, morpholin-4-ylmethyl, methoxymethoxymethyl, cyclopropyl, 1-azetidinylmethyl, 1-pyrrolidinylmethyl, or 1,3-dioxolan-2-yl;

$R^2$ is hydrogen or fluoro;
$R^3$ is hydrogen, chloro, or fluoro; provided that at least one of $R^2$ and $R^3$ is hydrogen;
$R^4$ is hydrogen, methyl, chloro, or fluoro; and
— is a single bond that is either present or absent; or a pharmaceutically acceptable salt thereof.

3. The compound of claim 1 wherein:
$R^1$ is dimethylaminomethyl, methylaminomethyl or aminomethyl;
$R^2$ is hydrogen, or fluoro; $R^3$ is hydrogen, chloro, or fluoro; provided that at least one of $R^2$ and $R^3$ is hydrogen;
$R^4$ is hydrogen, methyl, chloro, or fluoro; and
— is a single bond that is either present or absent; or a pharmaceutically acceptable salt thereof.

4. The compound of claim 1 wherein $R^1$ is dimethylaminomethyl, $R^2$ is hydrogen, $R^3$ is fluoro, and $R^4$ is fluoro; or a pharmaceutically acceptable salt thereof.

5. The compound of claim 1 wherein $R^1$ is methylaminomethyl, $R^2$ is hydrogen, $R^3$ is fluoro, and $R^4$ is fluoro; or a pharmaceutically acceptable salt thereof.

6. The compound of claim 1 wherein $R^1$ is aminomethyl, $R^2$ is hydrogen, $R^3$ is halo, and $R^4$ is halo; or a pharmaceutically acceptable salt thereof.

7. A compound selected from the group consisting of:
1-(2-{4-[7-(5-((Dimethylamino)methyl)-2-fluoro-pyridin-4-yl)benzo[b]thiophen-2-yl]-5-fluoropyrimidin-2-ylamino}ethyl)imidazolidin-2-one,
1-(2-{4-[7-(2-Fluoro-5-(morpholinomethyl)-pyridin-4-yl)benzo[b]thiophen-2-yl]pyrimidin-2-ylamino}ethyl)imidazolidin-2-one,
1-(2-{5-Fluoro-4-[7-(2-fluoro-5-(morpholinomethyl)pyridin-4-yl)benzo[b]thiophen-2-yl]-pyrimidin-2-ylamino}ethyl)imidazolidin-2-one,
1-(2-{4-[7-(5-((Dimethylamino)methyl)-2-fluoropyridin-4-yl)benzo[b]thiophen-2-yl]pyrimidin-2-ylamino}ethyl)imidazolidin-2-one,
1-(2-{5-Fluoro-4-[7-(3-(morpholinomethyl)-pyridin-4-yl)benzo[b]thiophen-2-yl]pyrimidin-2-ylamino}ethyl)imidazolidin-2-one,
1-(2-{4-[7-(5-(1,3-Dioxolan-2-yl)-2-fluoropyridin-4-yl)benzo[b]thiophen-2-yl]-5-fluoropyrimidin-2-ylamino}ethyl)imidazolidin-2-one,
1-(2-{5-Fluoro-4-[7-(2-fluoro-3-((methoxymethoxy)methyl)-pyridin-4-yl)benzo[b]thiophen-2-yl]pyrimidin-2-ylamino}ethyl)imidazolidin-2-one,
1-(2-{4-[7-(5-Cyclopropyl-2-fluoropyridin-4-yl)benzo[b]thiophen-2-yl]-5-fluoropyrimidin-2-ylamino}ethyl)imidazolidin-2-one, 1-(2-{5-Fluoro-4-[7-(2-fluoro-5-(pyrrolidin-1-ylmethyl)
pyridin-4-yl)benzo[b]thiophen-2-yl]pyrimidin-2-
ylamino}ethyl)imidazolidin-2-one,
1-(2-{4-[7-(5-Azetidin-1-ylmethyl)-2-fluoropyridin-4-yl)
benzo[b]thiophen-2-yl]-5-fluoropyrimidin-2-
ylamino}ethyl)imidazolidin-2-one,
1-(2-{5-Chloro-4-[7-(5-((dimethylamino)methyl)-2-fluo-
ropyridin-4-yl)benzo[b]thiophen-2-yl]pyrimidin-2-
ylamino}ethyl)imidazolidin-2-one,
1-{2-[5-Fluoro-4-(7-{2-fluoro-5-[(2-hydroxy-ethy-
lamino)-methyl]pyridin-4-yl}benzo[b]thiophen-2-yl)
pyrimidin-2-ylamino]ethyl}imidazolidin-2-one,
1-(2-{5-Fluoro-4-[7-(2-fluoro-5-((propylamino)methyl)
pyridin-4-yl)benzo[b]thiophen-2-yl]pyrimidin-2-
ylamino}ethyl)imidazolidin-2-one,
1-(2-(4-(7-(5-((Ethylamino)methyl)-2-fluoropyridin-4-
yl)benzo[b]thiophen-2-yl)-5-fluoropyrimidin-2-
ylamino)ethyl)imidazolidin-2-one,
1-{2-[4-(7-{5-[(Ethyl(methyl)amino)-methyl]-2-fluoro-
pyridin-4-yl}benzo[b]thiophen-2-yl]-5-fluoropyrimi-
din-2-ylamino}ethyl}imidazolidin-2-one,
1-(2-{4-[7-(5-((Diethylamino)methyl)-2-fluoropyridin-4-
yl)benzo[b]thiophen-2-yl]-5-fluoropyrimidin-2-
ylamino}ethyl)imidazolidin-2-one,
1-(2-{4-[7-(5-((Dimethylamino)methyl)-2-fluoropyridin-
4-yl)-benzo[b]thiophen-2-yl]-5-methylpyrimidin-2-
ylamino}ethyl)imidazolidine-2-one,
1-(2-{5-Fluoro-4-[7-(2-fluoro-5-((methylamino)methyl)
pyridin-4-yl)benzo[b]thiophen-2-yl]-pyrimidin-2-
ylamino}ethyl)imidazolidin-2-one,
1-(2-{4-[7-(2-Fluoro-5-((methylamino)methyl)pyridin-4-
yl)benzo[b]thiophen-2-yl]-5-methylpyrimidin-2-
ylamino}ethyl)imidazolidin-2-one,
1-(2-{5-Chloro-4-[7-(2-fluoro-5-((methylamino)methyl)
pyridin-4-yl)benzo[b]thiophen-2-yl]pyrimidin-2-
ylamino}ethyl)imidazolidin-2-one,
1-(2-{4-[7-(2-Fluoro-5-((methylamino)methyl)pyridin-4-
yl)benzo[b]thiophen-2-yl]pyrimidin-2-ylamino}ethyl)
imidazolidin-2-one,
1-[2-(4-{7-[5-(1-Aminoethyl)-2-fluoropyridin-4-yl]
benzo[b]thiophen-2-yl}-5-fluoropyrimidin-2-ylamino)
ethyl]imidazolidin-2-one,
1-(2-{5-Fluoro-4-[7-(2-fluoro-5-((methylamino)methyl)
pyridin-4-yl)benzo[b]thiophen-2-yl]pyrimidin-2-
ylamino}ethyl)-1H-imidazol-2(3H)-one,
1-{2-[5-Fluoro-4-(7-{2-fluoro-5-[3,3,3-trifluoro-propy-
lamino)-methyl]-pyridin-4-yl]benzo[b]thiophen-2-yl)
pyrimidin-2-ylamino}ethyl}imidazolidin-2-one,
3-{[6-Fluoro-4-(2-{5-fluoro-2-[2-(2-oxoimidazolidin-1-
yl)ethylamino]pyrimidin-4-yl}benzo[b]thiophen-7-yl)
pyridine-3-yl]methylamino}propanenitrile,
1-(2-{4-[7-(5-(Aminomethyl)-2-fluoropyridin-4-yl)
benzo[b]thiophen-2-yl]-5-fluoropyrimidin-2-
ylamino}ethyl)imidazolidin-2-one,
R-1-[2-(4-{7-[5-(1-Aminoethyl)-2-fluoropyridin-4-yl]
benzo[b]thiophen-2-yl}-5-fluoropyrimidin-2-ylamino)
ethyl]imidazolidin-2-one,
S-1-[2-(4-{7-[5-(1-Aminoethyl)-2-fluoropyridin-4-yl]
benzo[b]thiophen-2-yl}-5-fluoropyrimidin-2-ylamino)
ethyl]imidazolidin-2-one,
1-[2-(5-Fluoro-4-{7-[2-fluoro-5-(2-hydroxyethoxy)pyri-
din-4-yl]benzo[b]thiophen-2-yl}pyrimidin-2-ylamino)
ethyl]imidazolidin-2-one,
1-(2-(4-(7-(3-Ethynylpyridin-4-yl)benzo[b]thiophen-2-
yl)pyrimidin-2-ylamino)ethyl)imidazolidin-2-one,
1-(2-(4-(7-(3-Ethynylpyridin-4-yl)benzo[b]thiophen-2-
yl)-5-fluoropyrimidin-2-ylamino)ethyl)imidazolidin-2-
one,
1-(2-(4-(7-(5-(1-Aminoethyl)-2-chloropyridin-4-yl)
benzo[b]thiophen-2-yl)-5-fluoropyrimidin-2-ylamino)
ethyl)imidazolidin-2-one,
S-1-(2-(4-(7-(5-(1-(Ethylamino)ethyl)-2-fluoropyridin-4-
yl)benzo[b]thiophen-2-yl)-5-fluoropyrimidin-2-
ylamino)ethyl)imidazolidin-2-one,
R-1-(2-(4-(7-(5-(1-(Ethylamino)ethyl)-2-fluoropyridin-4-
yl)benzo[b]thiophen-2-yl)-5-fluoropyrimidin-2-
ylamino)ethyl)imidazolidin-2-one,
S-1-(2-(5-Fluoro-4-(7-(2-fluoro-5-(1-(methylamino)
ethyl)pyridin-4-yl)benzo[b]thiophen-2-yl)pyrimidin-2-
ylamino)ethyl)imidazolidin-2-one, and
R-1-(2-(5-Fluoro-4-(7-(2-fluoro-5-(1-(methylamino)
ethyl)pyridin-4-yl)benzo[b]thiophen-2-yl)pyrimidin-2-
ylamino)ethyl)imidazolidin-2-one; or a pharmaceuti-
cally acceptable salt.

8. A pharmaceutical composition comprising a compound of claim 1 or a pharmaceutically acceptable salt thereof, in combination with a pharmaceutically acceptable carrier, diluent or excipient.

* * * * *

UNITED STATES PATENT AND TRADEMARK OFFICE
CERTIFICATE OF CORRECTION

PATENT NO. : 8,063,212 B2  Page 1 of 1
APPLICATION NO. : 12/516251
DATED : November 22, 2011
INVENTOR(S) : Harold Burns Brooks et al.

It is certified that error appears in the above-identified patent and that said Letters Patent is hereby corrected as shown below:

Title Page, item (57) (Abstract), Column 2, line 14: Delete "or" and insert -- or a --, therefor.

At Column 47, Line 11: In Claim 7, delete "4-yl)" and insert -- 4-yl} --, therefor.

At Column 47, Line 21: In Claim 7, delete "ylamino}" and insert -- ylamino] --, therefor.

At Column 48, Line 2: In Claim 7, delete "4-yl]" and insert -- 4-yl} --, therefor.

At Column 48, Line 3: In Claim 7, delete "ylamino}" and insert -- ylamino] --, therefor.

Signed and Sealed this
Seventeenth Day of April, 2012

David J. Kappos
*Director of the United States Patent and Trademark Office*